US012747319B2

(12) United States Patent
Bansal et al.

(10) Patent No.: US 12,747,319 B2
(45) Date of Patent: Sep. 29, 2026

(54) POLYMER AND COMPOSITION FROM RENEWABLE SOURCE

(71) Applicant: ÅBO AKADEMI UNIVERSITY, Turku (FI)

(72) Inventors: Kuldeep Kumar Bansal, Turku (FI); Jessica Rosenholm, Turku (FI); Ari Rosling, Turku (FI)

(73) Assignee: ÅBO AKADEMI UNIVERSITY, Turku (FI)

( * ) Notice: Subject to any disclaimer, the term of this patent is extended or adjusted under 35 U.S.C. 154(b) by 1153 days.

(21) Appl. No.: 17/641,285

(22) PCT Filed: Sep. 10, 2020

(86) PCT No.: PCT/FI2020/050579
§ 371 (c)(1),
(2) Date: Mar. 8, 2022

(87) PCT Pub. No.: WO2021/048469
PCT Pub. Date: Mar. 18, 2021

(65) Prior Publication Data

US 2022/0289903 A1 Sep. 15, 2022

(30) Foreign Application Priority Data

Sep. 10, 2019 (FI) ..................................... 20195748

(51) Int. Cl.
*C08G 63/08* (2006.01)
*A61K 31/337* (2006.01)
(Continued)

(52) U.S. Cl.
CPC ............ *C08G 63/08* (2013.01); *A61K 31/337* (2013.01); *A61K 31/65* (2013.01); *A61K 47/59* (2017.08);
(Continued)

(58) Field of Classification Search
None
See application file for complete search history.

(56) References Cited

U.S. PATENT DOCUMENTS 7,018,655 B2 3/2006 Lele et al.
8,420,067 B2 4/2013 Krippner et al.
(Continued)

FOREIGN PATENT DOCUMENTS

CN 103764708 4/2014
JP 2001-517603 10/2001
(Continued)

OTHER PUBLICATIONS

International Search Report for PCT/FI2020/050579, mailed Nov. 20, 2020, 4 pages.
(Continued)

*Primary Examiner* — Rachel Kahn
(74) *Attorney, Agent, or Firm* — Nixon & Vanderhye PC

(57) ABSTRACT

The present invention relates to polymers, compositions thereof, and methods of producing polymers in general. Furthermore, the present invention relates to pharmaceutical compositions and uses of said polymers, compositions and pharmaceutical compositions. More particular, the present invention relates to polymers of jasmine lactone, where pendant groups of said polymers can readily be used for attaching functional moieties comprising active agents. Furthermore, the present invention relates to modified jasmine lactones that can readily be used in methods of producing polymers of the present invention. More particular, the invention relates to polymers from renewable monomers, which can be used in applications such as drug delivery and diagnosis, polymer-drug conjugates, medical devices, cosmetic products, polymers with marker unit, polymers usable
(Continued)

as flame retardants, tissue engineering, coatings, paints, lubricants and biodegradable plastics.

27 Claims, 6 Drawing Sheets

(51) Int. Cl.

| | |
|---|---|
| ***A61K 31/65*** | (2006.01) |
| ***A61K 47/59*** | (2017.01) |
| ***C08G 63/664*** | (2006.01) |
| ***C08G 63/685*** | (2006.01) |
| ***C08G 63/688*** | (2006.01) |

(52) U.S. Cl.
CPC ....... *C08G 63/664* (2013.01); *C08G 63/6852* (2013.01); *C08G 63/6882* (2013.01)

(56) References Cited

U.S. PATENT DOCUMENTS

| | | | | |
|---|---|---|---|---|
| 8,734,846 | B2 | 5/2014 | Ali et al. | |
| 2003/0181613 | A1 | 9/2003 | Lele et al. | |
| 2009/0304767 | A1* | 12/2009 | Sikes | A61L 31/16 525/411 |
| 2015/0307656 | A1* | 10/2015 | Dagorne | C08G 64/30 549/206 |

FOREIGN PATENT DOCUMENTS

| | | |
|---|---|---|
| JP | 2009-530447 | 8/2009 |
| JP | 2013-213186 | 10/2013 |
| JP | 6051856 | 12/2016 |
| JP | 2017-504573 | 2/2017 |
| WO | 2014/087020 | 6/2014 |

OTHER PUBLICATIONS

Written Opinion of the ISA for PCT/FI2020/050579, mailed Nov. 20, 2020, 5 pages.

Search Report for FI20195748, dated Apr. 6, 2020, 2 pages.

Bansal et al., New biomaterials from renewable resources—amphiphilic block copolymers from [delta]-decalactone, Polymer Chemistry, vol. 6, No. 40, Jan. 1, 2015, pp. 7196-7210.

Mikhail et al., 11 Poly(ethylene glycol)-b-poly([epsilon]-caprolactone) Micelles Containing Chemically Conjugated and Physically Entrapped Docetaxel: Synthesis, Characterization, and the Influence of the Drug on Micelle Morphology, Biomacromolecules, vol. 11, No. 5, May 10, 2010, pp. 1273-1280.

Lardelli et al., Synthesis of lactones. I. Saturated δ-and ε-lactones. In: Recueil des Travaux Chimiques des pays-Bas in English, Feb. 16, 1967, vol. 86, No. 5, pp. 481-503.

Demole et al., Synthèse du cis-(pentèn-2-yl)-5-pentanolide-(5,1), composant odorant de jasmin (*Jasminum grandiflorum* L.). In: Helvetica Chimica Acta 1962, vol. 45, No. 4, pp. 1256-1261.

Coyle et al., "Phase I study of BAY 94-9027, a PEGylated B-domain-deleted recombinant factor VIII with an extended half-life, in subjects with hemophilia A", Journal of Thrombosis and Haemostasis, 2014, 12, pp. 488-496.

Apr. 14, 2023 Office Action issued in Japanese Patent Application No. 2022-515102, pp. 1-2 [machine translation included].

* cited by examiner

POLYMER AND COMPOSITION FROM RENEWABLE SOURCE

This application is the U.S. national phase of International Application No. PCT/FI2020/050579 filed Sep. 10, 2020 which designated the U.S. and claims priority to FI 20195748 filed Sep. 10, 2019, the entire contents of each of which are hereby incorporated by reference.

FIELD OF THE INVENTION

The present invention relates to polymers, compositions thereof, and methods of producing polymers in general. Furthermore, the present invention relates to pharmaceutical compositions and uses of said polymers, compositions and pharmaceutical compositions. More particular, the present invention relates to polymers of jasmine lactone, which pendant groups of said polymers can readily be used for attaching functional moieties comprising active agents. Furthermore, the present invention relates to modified jasmine lactones that can readily to be used in methods of producing polymers of the present invention. More particular, the invention relates to polymers from renewable monomers, which can be used in applications such as drug delivery and diagnosis, polymer-drug conjugates, medical devices, cosmetic products, polymers with marker unit, polymers usable as flame retardants, tissue engineering, coatings, paints, lubricants and biodegradable plastics.

BACKGROUND OF THE INVENTION

Polymers are widely used advance material, which are found almost in every material used in our daily life. Polymers found application in different domains of sciences, technologies and industries, including various fibres and bio-medical applications, such as implants, medical devices, and drug delivery.

Currently used polymers are mainly fossil fuel-based and therefore, greener alternatives are needed. Biobased polymers are derived from renewable biomass sources, however, all these polymers are not environmentally friendly. Therefore, in addition to which sources used in the production of polymers, the biodegradation of the polymers used in various applications is a central and worldwide issue that still need to be undertaken. For example, the time-frame for a conventional non-biodegradable plastic bag to break down in the terrestrial environment is 500 years or more. However, there are examples of (synthetic) polymers that biodegrade faster, e.g. polycaprolactone, poly-3-hydroxybutyrate, polylactic acid, and cellulose acetate. Biodegradable polymers have found a large variety of applications, e.g. in biomedicine and more especially in targeted drug delivery systems. However, there are still a lack of simplicity in polymer designs and broad applicability of single material or approach. In addition, a simplistic design of a biodegradable polymer with the scope of tunability as per desired application, reproducibility and use of economical renewable feedstock in the production of polymers are key qualities that are still missing from currently used biodegradable polymers.

Polymer-drug conjugates have demonstrated their superior efficacy and approximately ten of such formulations are in clinical trials. Conjugates based on poly(ethylene glycol) (PEG) are already in market such as Adagen® (PEG-adenosine deaminase protein) and Movantik® (PEG-naloxone). In addition, a reported polymer drug conjugate that is in market or in clinical trials include Jivi® that is a conjugation of B-domain-deleted recombinant factor VIII with PEG [Coyle et al., Phase I study of BAY 94-9027, a PEGylated B-domain-deleted recombinant factor VIII with an extended half-life, in subjects with hemophilia A, *Journal of Thrombosis and Haemostasis,* 2014, 12, 488-496]. Jivi® is an injectable medicine used to replace clotting factor (Factor VIII or antihemophilic factor) that is missing in people with haemophilia A. However, non-degradability and lack of functional moieties (type and number) associated with PEG limits its applications. Further, achieving high drug loading, combination therapy, insertion of targeting ligand and contrasting agent in a single nanocarrier is rather challenging using PEG as a key polymer.

Further, DEP® docetaxel is a conjugate of docetaxel with polylysine dendrimer and is in phase II trials for the treatment of solid tumours [U.S. Pat. No. 8,420,067B2]. NK012®, a conjugate of SN38 (7-ethyl-10-hydroxy-campto-thecin) with PEG-b-poly(glutamic acid) copolymer, where poly(glutamic acid) was used as attaching site, is another example of polymer drug conjugate [U.S. Pat. No. 8,734,846B2]. Furthermore, conjugation of paclitaxel and doxorubicin to polylactic acid (PLA) using its block copolymer mPEG-b-PLA has been reported [U.S. Pat. No. 7,018, 655B2].

Efforts has been made to create better alternatives to fossil fuel-based polymers but, reported methods used to insert functional moieties of choice in a polymeric chain are tedious and expensive. Therefore, there is a need of novel biodegradable and functional polymers that can be produced with minimal efforts. In addition, novel polymers, which can be synthesized using monomers obtained from renewable resources as green alternatives to fossil fuel-based polymers, are urgently needed.

BRIEF DESCRIPTION OF THE INVENTION

An object of the present invention is thus to provide novel polymers and compositions so as to overcome the above problems. The objects of the invention are achieved by a polymer, a composition, and a pharmaceutical composition as characterized by what is stated in the independent claims. The preferred embodiments of the invention are disclosed in the dependent claims.

An object of the present invention is thus to provide novel polymers that are formed from renewable resources. A further object of the present invention is to provide polymers usable for conjugating active agents to the polymers.

The present invention accordingly provides novel polymers comprising at least one repeating unit, wherein the at least one repeating unit has Formula [I]

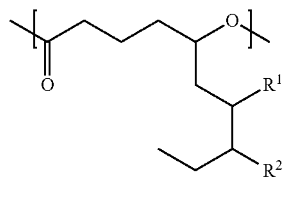

[I]

or a salt thereof, wherein R1 and R2 are as defined in the claims.

A further aspect of the current invention is to provide novel compositions comprising a polymer of Formula [I] and at least one active agent, or salts thereof, wherein R1 and R2 are as defined in the claims.

A yet further aspect of the current invention is to provide methods for producing polymers according to the invention.

A yet further aspect of the current invention is to provide pharmaceutical compositions comprising one or more polymer of Formula [I] or an effective amount of one or more compositions as defined in the claims in combination with one or more other active ingredients, wherein the salt is a pharmaceutically acceptable salt, optionally together with one or more pharmaceutically acceptable excipient(s).

Still further aspect of the current invention is to provide uses of the novel polymers, compositions and pharmaceutical compositions according to the claims.

The invention is based on the surprising realization and finding that novel biodegradable polymers of jasmine lactone can be produced from jasmine lactone or derivatives thereof as disclosed in the present invention. Therefore, an advantage of the invention is that the novel polymers can be produced from a renewable sources as green alternatives to fossil fuel-based polymers. A further surprising realization and advantage of the current invention is that the polymers comprise versatile possibilities of attaching active agents to the polymers. Yet a further advantage of the present invention is that the novel polymers comprise low to high loadings of active agents to the polymers.

Moreover, the present application surprisingly discloses that compositions of drug-polymer conjugates of the present invention show stimuli responsive drug release of the conjugated drugs. A further advantage of the compositions of drug-polymer conjugates of the present invention is that they differentiate between normal and cancer cells thus resulting in lower toxicity to normal cells compared to cancer cells thus producing fewer side effects. Yet a further surprising finding and advantage of the present invention is that the survivability of mice when treated with the invention was increased.

BRIEF DESCRIPTION OF THE DRAWINGS

In the following the invention will be described in greater detail by means of preferred embodiments with reference to the attached [accompanying] drawings, in which

FIG. 2*a* indicates the mPEG-b-PJL-S-S-DOX (1dx') is polydisperse with mean size less than 150 nm (peak 1: size (d.nm) of 59.64% volume of 64.5, and st. dev. (d.nm) of 21.97; peak 2: size (d.nm) of 293.8, % volume of 35.5, and st. dev. (d.nm) of 136.4; Z-average (d.nm) of 158.8 and PdI of 0.292).

DETAILED DESCRIPTION OF THE INVENTION

Figure 1:
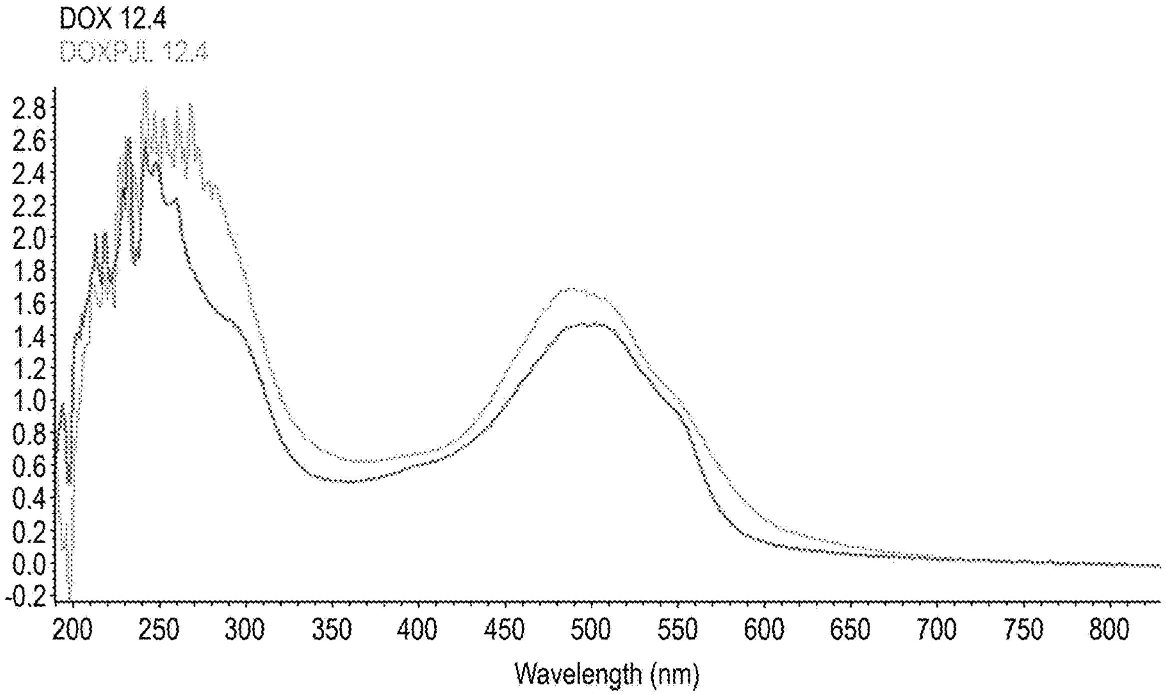
FIG. 1 illustrates an example of overlapped UV-Vis spectra of doxorubicin HCl (DOX, black spectrum) and DOX-conjugate mPEG-b-PJL-S-S-DOX (1dx', DOX-PJL, fade spectrum) (wavelength (nm) vs absorbance).

The present invention relates to polymers comprising at least one repeating unit, wherein the at least one repeating unit has Formula [I]

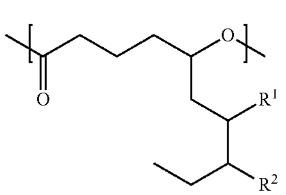

[I]

or a salt thereof, wherein R1 and R2 are as defined in the claims. The invention is based on the surprising realization and finding that novel biodegradable polymers of jasmine lactone can be produced from jasmine lactone or derivatives thereof as disclosed in the present invention. Therefore, an advantage of the invention is that the novel polymers can be produced from a renewable sources as green alternatives to fossil fuel-based polymers. A further surprising realization and advantage of the current invention is that the polymers comprise versatile possibilities of attaching active agents to the polymers. Yet a further advantage of the present invention is that the novel polymers comprise low to high loadings of active agents to the polymers.

Moreover, the present application surprisingly discloses that compositions of drug-polymer conjugates of the present invention show stimuli responsive drug release of the conjugated drugs. A further advantage of the compositions of drug-polymer conjugates of the present invention is that they differentiate between normal and cancer cells thus resulting in lower toxicity to normal cells compared to cancer cells thus producing fewer side effects. Yet a further surprising finding and advantage of the present invention is that the survivability of mice when treated with the invention was increased.

The objective of the present invention is thus to provide polymers comprising at least one repeating unit, which has Formula [I]. In an aspect of the present invention the polymers of the invention comprise versatile possibilities of attaching active agents to the polymers. The polymers of the invention can be modified with suitable linkers that can be used to conjugate active ingredients to form compositions of active agent-conjugated polymers of the invention. In addition, active agents may be directly attached to the polymers of the invention.

Another objective of the present invention is to provide modified jasmine lactones of the present invention. In one aspect of the present invention the modified jasmine lactones can be polymerized to form polymers of the present invention.

Another objective of the present invention is to provide active agent functionalized jasmine lactones of the present invention. In one aspect of the present invention the functionalized jasmine lactones can be polymerized to form compositions of the present invention.

Yet another objective is to provide pharmaceutical compositions of the present invention. Polymers of the present invention can be modified and/or functionalized with active agents to form compositions and pharmaceutical compositions of the present invention. Said pharmaceutical compositions may be used for as a medicament.

The following embodiments are exemplary. Although the specification may refer to “an”, “one”, or “some” embodiment(s) in several locations, this does not necessarily mean that each such reference is to the same embodiment(s), or that the feature only applies to a single embodiment. Single features of different embodiments may also be combined to provide other embodiments. Furthermore, words “comprising”, “containing” and “including” should be understood as not limiting the described embodiments to consist of only those features that have been mentioned and such embodiments may contain also features/structures that have not been specifically mentioned.

The term “polymer” as used herein and hereafter refers to natural and/or synthetic linear or two- or three-dimensional homopolymers and copolymers that can be unbranched or branched polymers, such as, but not limited to, star polymers, comb polymers, brush polymers, dendronized polymers, ladder polymers, and dendrimers. Polymers which contain only a single type of repeating unit are referred as homopolymers, while polymers containing two or more types of repeating units are referred as copolymers. Copolymers include, but are not limited to, alternating copolymers, periodic copolymers, statistical copolymers, random copolymers, block copolymers and graft copolymers.

The term “copolymer” as used herein and hereafter refers to polymers derived from more than one species of monomer.

The term “monomer” as used herein and hereafter refers to molecule that can undergo polymerization thereby contributing constitutional units to the essential structure of a polymer. The monomers are used to form the one or more repeating units of the polymer. Monomers include, but are not limited to, lactones, carbonates, esters, lactams, alkenes and epoxides. Examples of preferred monomers include, but are not limited to, jasmine lactone, lactide, glycolide, caprolactone, decalactone, butyrolactone, pentadecalactone, hydroxybutanoate, ethylene, ethylene oxide, ethylene carbonate, and caprolactam.

The term “repeating unit” as used herein and hereafter refers to a part of the main chain (backbone) of a polymer that is connected on at least two ends to the polymer chain. I.e. the repeating unit is a part of a polymer whose repetition would produce the complete polymer chain (except for the end-groups) by linking the repeat units together successively along the chain. Furthermore, a repeating unit is a basic structural unit of a polymer, said repeating unit corresponds to a monomer unit, which has been polymerized to produce a polymer.

The term “$C_{1-20}$-alkyl” as used herein and hereafter as such or as part of haloalkyl, perhaloalkyl or alkoxy group is an aliphatic linear, branched or cyclic, especially linear or branched, hydrocarbon group having the indicated number of carbon atoms, for example $C_{1-20}$-alkyl has 1 to 20 carbon atoms in the alkyl moiety and thus, for example, $C_{1-3}$-alkyl includes methyl, ethyl, n-propyl, isopropyl, and $C_{1-6}$-alkyl additionally includes branched and straight chain n-butyl, sec-butyl, isobutyl, tert-butyl, pentyl and hexyl. The said hydrocarbon group having suitably 1 to 20, preferably 1 to 7, carbon atoms in the alkyl moiety. Examples of aliphatic cyclic hydrocarbon groups include, but are not limited to, cyclopropyl, and cyclohexyl.

The term "$C_{2-20}$-alkenyl" as used herein and hereafter is an unsaturated linear or branched hydrocarbon group having at least one olefinic double bond between any two carbon atoms and having suitably 2 to 20, preferably 2 to 7, carbon atoms in the alkenyl moiety, such as ethenyl, 1-propenyl, 2-propenyl, 3-propenyl, butenyl, pentenyl, and hexenyl. Examples of preferred alkenyls groups include, but are not limited to, linear alkenyl groups having a terminal double bond such as vinyl and allyl groups.

The term "$C_{2-20}$-alkynyl" as used herein is an unsaturated linear or branched hydrocarbon group having at least one olefinic triple bond between any to two carbon atoms and having suitably 2 to 20, preferably 2 to 7, carbon atoms in the alkenyl moiety, such as ethynyl, propynyl, butynyl, pentynyl, and hexynyl.

The term "$C_{1-10}$-alkylenyl" as used herein and hereafter, is a divalent group derived from a straight or branched chain hydrocarbon of having suitably 1 to 10 carbon atoms. Representative examples of an alkylenyl group include, but are not limited to, $—CH_2—$, $—CH(CH_3)—$, $—C(CH_3)_2—$, $—CH_2CH_2—$, $—CH_2CH_2CH_2—$, $—CH_2CH_2CH_2CH_2—$, and $—CH_2CH(CH_3)CH_2—$.

The term "haloalkyl" as used herein and hereafter refers to any of the above alkyl groups where one or more hydrogen atoms are replaced by halogen(s): in particular I, Br, F or Cl. Examples of haloalkyl groups include without limitation chloromethyl, fluoromethyl, $—CH_2CF_3$, trifluoromethyl ($—CF_3$) and tri-chloromethyl ($—CCl_{13}$).

The term "halogen" as used herein and hereafter by itself or as part of other groups refers to the Group VIIa elements and includes F, Cl, Br and I.

The term "saturated or partly unsaturated mono-, bi-, tri- or tetracyclic cycloalkyl" as used herein and hereafter refers to cycloalkyl groups having 3 to 30 carbon atoms and thus includes, but are not limited to, cyclopropyl, cyclobutyl, cyclopentyl, cyclohexyl, cycloheptyl, trans-cyclooctene, cyclooctyne, bicyclo-[2.2.1]heptyl, bicyclo[2.2.1]heptenyl, 1,4-diazabicyclo[2.2.2]octanyl, bicyclo-[4.4.0]decanyl, and perhydrocyclopenta[a]phenanthrenyl. It is to be understood that the cycloalkyl can be a spirocyclic, fused bicyclic or a bridged bicyclic compound.

The term "a saturated or partly unsaturated mono-, bi-, tri- or tetracyclic heterocycle" used herein and refers to aliphatic or partly unsaturated ring(s) having one or more heteroatoms, preferably 1 to 12 heteroatoms, as ring atoms, where the said heteroatoms include at least the heteroatoms denoted in the same context and optionally one or more further heteroatom(s). Each heteroatom is independently selected from N, S, O, P, Si and Se preferably from N, O and S, unless denoted otherwise. Examples of saturated monocyclic heterocycles include, but are not limited to, pyrrolidinyl, tetrahydrofuranyl, imidazolidinyl, pyrazolidinyl, piperidinyl, tetrahydropyranyl, tetrahydrothiopyranyl, piperazinyl, morpholinyl, thiomorpholinyl, dioxanyl, oxiranyl, and dithianyl. It is to be understood that the heterocycle can be a spirocyclic, fused bicyclic or a bridged bicyclic compound.

The term "optionally substituted" as used herein and hereafter denotes that the group it refers to is either unsubstituted or substituted independently with one or more, preferably 1, 2, 3 or 4, substituent(s) attached at any available atom to produce a stable compound. E.g. phenyl may be substituted once with a denoted substituent attached to o-, m- or p-position of the phenyl ring. In general, "substituted" refers to a substituent group as defined herein in which one or more bonds to a hydrogen atom contained therein are replaced by a bond to a non-hydrogen atom unless otherwise denoted. The substituent groups are each independently selected from the group consisting of halogen, $CO_2H$ and esters thereof; $C_{1-4}$-alkyl, in particular methyl; OH, and ethers thereof; $NO_2$, $N_3$, NOH, and ethers thereof; CN, $NH_2$, and amides thereof; SH, and thioethers thereof; SC(O)—$C_{1-6}$-alkyl, OC(O)—$C_{1-6}$-alkyl, NHC(O)—$C_{1-6}$-alkyl, NHC(O)NH—$C_{1-6}$-alkyl, NHC(O)O—$C_{1-6}$-alkyl, $C_{1-10}$-alkyl, $C_{2-10}$-alkenyl, $C_{2-10}$-alkynyl, $C_{1-5}$-haloalkyl, $C_{1-4}$alkoxy, in particular methoxy; and acetoxy. Preferably said substituent group is optionally substituted with OH, $NH_2$, $CO_2H$ and halogen.

"Optional" or "optionally" denotes that the subsequently described event or circumstance may but need not occur, and that the description includes instances where the event or circumstance occurs and instances in which it does not. "Comprises" or "comprising" denotes that the subsequently described set may but need not include other elements.

The term "aryl" used herein and hereafter refers to mono- and polycyclic aromatic hydrocarbons. Examples of aryls include, but are not limited to, phenyl and naphtalenyl. The aryl can be substituted with one or more substituents as defined herein and hereafter.

The term "heteroaryl" used herein and hereafter refers to a mono- and polycyclic aromatic ring comprising one or more heteroatoms, preferably 1 to 12 heteroatoms, as ring atoms, where the said heteroatoms include at least the heteroatoms denoted in the same context and optionally one or more further heteroatom(s). Each heteroatom is independently selected form N, O, S, P, Si, and Se, preferably from N, O and S, unless denoted otherwise. The heteroaryl group need only have some degree of aromatic character. The heteroaryl can be substituted with one or more substituents as defined herein and hereafter. Examples of monocyclic heteroaryls include, but are not limited to, pyrrolyl, furyl, thienyl, phospholyl, silolyl, triazolyl, furazanyl, oxadiazolyl, thiadiazolyl, dithiazolyl, tetrazolyl, imidazolyl, pyridinyl, pyranyl, thiopyranyl, salinyl, phosphinine, pyrazinyl, pyrimidinyl, pyridazinyl, oxazine, thiazine, diozine, dithiine, triazinyl, and tetrazinyl. Examples of bicyclic heteroaryls include indolyl, quinolinyl, benzoazepinyl, benzothiazolyl and other bicyclic aryls resulting from the fusion of a monocyclic heteroaryl and benzene ring or another monocyclic heteroaryl. Examples of tricyclic heteroaryls include carbazolyl, acridinyl, other tricyclic aryls resulting from the fusion of a bicyclic heteroaryl as defined above and a benzene ring or another monocyclic heteroaryl.

The definition "—N(O═CC═C)C═O" used herein and hereafter refers to a maleimide group, which may be attached to the polymer or jasmine lactone via it's nitrogen atom via a bond, a linker group (L) or a heteroatom, such as O, S or N, i.e. the maleimide group may be N-substituted with a suitable divalent group, such as a $C_{1-10}$-alkylenyl, a divalent poly(ethylene) group, or another linker group (L) as defined herein and hereafter, which can be attached to the monomer or the polymer. Examples of a maleimide group with linker groups include, but are not limited to, 2,5-dioxo-2,5-dihydropyrrol-1-ide:

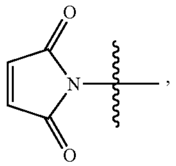 [SMILES: *N1C(=O)C=CC1=O]

4-(2,5-dioxo-2,5-dihydro-1H-pyrrol-1-yl)-1-oxobutan-1-ide:

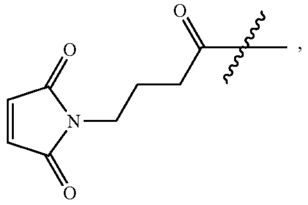

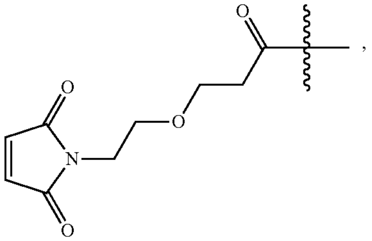

1-propyl-1H-pyrrole-2,5-dione:

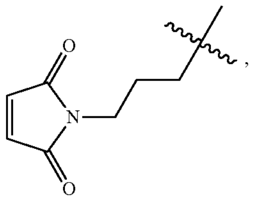 [SMILES: *CCCN1C(=O)C=CC1=O]

wherein the  defines the attachment of the maleimide group, with or without a linker group, to the polymer or the jasmine lactone. An example of a maleimide group, which is attached via a linker group to a polymer of the invention is presented in the structure below:

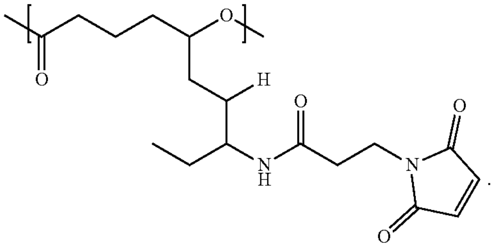

When any variable occurs more than one time in any constituent or in Formula [I], Formula [II] or Formula [xy] its definition on each occurrence is independent of its definition at every other occurrence. Further, combinations of substituents and/or variables are permissible only if such combination results a stable compound.

The definition "functional moiety" used herein and hereafter refers to a chemical moiety that may be attached, covalently or with ionic bond(s), to the polymer or the jasmine lactone of the invention. Functional moieties include, but to are not limited to, active agents and linker groups.

The term "composition" used herein and hereafter refers to a chemical substance and also to a mixture of at least two chemical substances. A composition of a chemical substance may comprise a polymer of the invention and at least one active agent(s). Therefore, said at least one active agent(s) may be covalently attached to a polymer of the invention, or said at least one active agent(s) may form ionic bond(s) with the polymer of the invention. It is to be understood that a composition of the invention may also comprise a mixture of said at least one active agent(s) and a polymer of the invention.

The term "active agent" used herein and hereafter refers to at least one molecule that exhibit a desired property that is useful in different applications. Examples of active agents include, but are not limited to, active ingredients, active pharmaceutical ingredients, antibodies, aptamers, units having fluorescence, radioactive or any other properties which can be detected, proteins, peptides, and flame retardants, and any derivatives thereof. Said active agent may be chemically modified to react with the polymers or jasmine lactones of the invention. Examples of active agents include, but are not limited to, ADA, anti-PDGFB aptamer, TLR7/TLR8 agonist, paclitaxel, neocarzinostatin, hyaluronidase, alendronate, cyclic peptide complement C3 inhibitor, L-asparaginase, human growth hormone, oxaliplatin, camptothecin, interferon α2b, IL-10, amifostine, SN-38, interferon α2a, arginine deiminase, rotigotine, irinotecan, G-CSF, arginase 1, somatostatin, cabazitaxel, HGH receptor antagonist, uricase, Pt(II), μ-opioid receptor agonist, anti-VEGF aptamer, carboxyhaemoglobin, TrkA inhibitor, loxenatide, epoetin beta, anti-CD40L Fab', docetaxel, anti-CXCL12 aptamer, anti-TNF Fab', aptamer complement C5 inhibitor, epirubicin, FGF21, phenylalanine ammonia lyase, IL-2, cisplatin, asparaginase, interferon β1a, recombinant factor VIII Fc-von Willebrand factor, factor VIII, naloxone, and tracing dyes, such as FITC, Rhodamine, TRITC, transferrin, folic acid and DNA, and any derivatives thereof.

The term "active pharmaceutical ingredient" used herein and hereafter refers to the ingredient in a pharmaceutical drug or pesticide that is biologically active. Said active pharmaceutical ingredient may be chemically modified to react with the polymers or jasmine lactones of the invention. Examples of active pharmaceutical ingredients include, but are not limited to, doxorubicin, daunorubicin, epirubicin, paclitaxel, docetaxel, cabazitaxel, camptothecin, cisplatin, oxaliplatin, docetaxel, gemcitabine, irinotecan, carboplatin, cetuximab, pemetrexed, bortezomib, topotecan, azacitidine, vinorelbine, mitoxantrone, fludarabine, alemtuzumab, carmustine, ifosfamide, idarubicin, mitomycin, fluorouracil, rituximab, trastuzumab, cetuximab, bevacizumab, methotrexate, melphalan, arsenic, denileukin diftitox, cytarabine, calcium levofolinate, cyclophosphamide, etoposide, viscum album, mesna, gemtuzumab, ozogamicin, busulfan, pentostatin, cladribine, bleomycin, daunorubicin, bendamustine, dacarbazine, raltitrexed, vincristine, mitoxantrone fotemustine, etoposide phosphate, porfimer sodium, ciprofloxacin, amoxicillin, ampicillin, kanamycin and vinblastine, and any derivatives thereof.

The active pharmaceutical ingredients may be a combination of any two or more of different active pharmaceutical ingredient categories, exemplified as anabolic agents, anaesthetics, analgesics, anti-acid agents, anti-arthritic agents, antibodies, anti-convulsants, anti-fungals, anti-histamines, anti-infectives, anti-inflammatories, anti-microbials, anti-mitotics, anti-parasitic agents, anti-protozoals, anti-ulcer agents, antiviral pharmaceuticals, behaviour modification drugs, biologicals, blood and blood substitutes, bronchodilators and expectorants, photosensitizing agents, cancer therapy and related pharmaceuticals, cardiovascular pharmaceuticals, central nervous system pharmaceuticals, diuretics, contraceptives, growth hormones, diabetes therapies, hematinics, fertility pharmaceuticals, hormone replacement therapies, growth promoters, immune suppressives, hemostatics, hormones and analogs, immunostimulants, minerals, muscle relaxants, nutraceuticals and nutritionals, natural products, ophthalmic pharmaceuticals, obesity therapeutics, pain therapeutics, osteoporosis drugs, proteins, peptides and polypeptides, retinoids, respiratory pharmaceuticals, sedatives and tranquilizers, transplantation products, urinary acidifiers, steroids, vitamins, and vaccines and adjuvants, and/or anti-tumour agents listed above, either as a single entity where appropriate, or as separate functional moieties. Exemplary combinations include, but are not limited to, combinations of: chemotherapeutic pharmaceuticals; anti-inflammatory pharmaceuticals and anti-arthritic pharmaceuticals; obesity therapeutics and diabetes therapeutics; growth hormones and growth promoters; muscle relaxants and anti-inflammatories; respiratory pharmaceuticals and bronchodilators or anti-microbials; chemotherapeutics and vitamins and the like.

Another group of pharmaceutically active agents contemplated herein are molecules or residues thereof which in themselves may not necessarily provide any desired or meaningful physiological activity but when attached to the surface or core of the polymer or when administered in combination (either separately, sequentially, or as an intimate composition) with one or more other pharmaceutically active agents, impart a physiological effect.

The term "aptamer" used herein and hereafter refers to oligonucleotides or peptide molecules that bind to a specific target molecule. Said aptamer may be chemically modified to react with the polymers or jasmine lactones of the invention. Target molecules include, but are not limited to, lysozyme, thrombin, human immunodeficiency virus trans-acting responsive element (HIV TAR), he-min, interferon $\gamma$, vascular endothelial growth factor (VEGF), prostate specific antigen (PSA), dopamine, and heat shock factor 1 (HSF1), and derivatives thereof.

The term "units having fluorescence, radioactive or any other properties which can be detected" used herein and hereafter refers to molecules that exhibit properties that can be utilized to detect said molecules. Said units may be chemically modified to react with the polymers or jasmine lactones of the invention. Properties that can be detected include, but are not limited to, fluorescence, radioactivity, and luminescence. Examples of units include, but are not limited to, fluorescein and derivatives and analogues thereof (such as fluorescein isothiocyanate (FITC)), eosin and derivatives and analogues thereof, rhodamine, doxorubicin, Cy3, Cy5, green fluorescent protein (GFP), fludeoxyglucose ([$^{18}$F]FDG) and fluorodopa ([$^{18}$F]6-fluoro-L-DOPA). Applications of said units include, but are not limited to, medicine, chemical sensors, biological detectors, labelling of molecules, and dyes, and any derivatives thereof.

The term "protein" used herein and hereafter refers to a molecule comprising more than 50 amino acid monomers covalently attached to each other by peptide bonds. Said protein may be chemically modified to react with the polymers or jasmine lactones of the invention. Examples of proteins include, but are not limited to, interferon, hyaluronidase, asparaginase, epoetin beta, and factor VIII (FVIII or anti-hemophilic factor (AHF)), and any derivatives thereof.

The term "peptide" used herein and hereafter refers to a molecule comprising up to 50 amino acids covalently attached to each other by peptide bonds. Said peptide may be chemically modified to react with the polymers or jasmine lactones of the invention. Examples of peptides include, but are not limited to, substance P (SP), glucagon, growth hormone releasing hormone (GHRH), and neurokinin A (substance K), and any derivatives thereof.

The term "flame retardant" used herein and hereafter refers to a molecule, which is used in combination with a material to improve the flame retardant properties of the material. Said flame retardant may or may not be chemically modified to react or interact with the polymers or jasmine lactones of the invention. For example, phosphorous and nitrogen-based flame retardants that can react or interact with double bonds, hydroxyl-, amine-, carboxylic ester- and carboxylic acid groups of the polymers and jasmine lactones of the invention are considered as potential compounds to modify and provide flame retardant properties of the jasmine lactones, polymers, and compositions of the invention. Both inorganic and organic molecules can be used as flame retardants; examples of flame retardants include, but are not limited to, halogenated hydrocarbons, phosphorous containing compounds, metallic compounds, hydroxides, and melamine derivatives. Examples of flame retardants include, but are not limited to, 2-carboxyethyl phenylphosphinic acid (CEPPA), phosphoric acid ($H_3PO_4$), phosphorous acid ($H_3PO_3$) and esters thereof, such as triphenylphosphate, tri-ethylphosphate, and 3-((diethoxyphosphoryl)oxy)-2-hydroxypropyl methacrylate; methacrylated phenolic melamine (MAPM), 9,10-dihydro-9-oxa-10-phosphaphenanthrene-10-oxide (DOPO) and derivatives thereof, such as 3-(6-oxidodibenzo[c,e][1,2]oxaphosphinin-6-yl)dihydrofuran-2,5-dione (DOPO-MAH) and 2-(6-oxido-6H-dibenzo[c,e][1,2]oxaphosphorin-6-yl)1,4-benzenediol (DOPO-HQ); tris(2,3-dibromopropyl) phosphate, and tetrabromobisphenol, and any derivatives thereof.

It is to be understood that one or more active agent(s) can be conjugated, encapsulated or adsorbed onto polymers or compositions of the invention. As used herein, said one or more active agent(s) may be covalently attached to the backbone of the polymer, a pendant group of the polymer, or a crosslink of the polymer thus forming a conjugate of the polymer and the active agent.

Furthermore, active agent(s) can be attached to the side group of jasmine lactone, modified jasmine lactone or to the backbone, pendant group or crosslink of the polymers via one or more ionic bonds. It is to be understood that with ionic bonds are meant bonds that involve electrostatic attraction between ions of opposite charges, e.g. $Na^+$ and $Cl^-$, $NH_4^+$ and $SO_4^{2-}$, and organic ammonium ions and carboxylate anions. Further, ionic bonds include, but are not limited to, salt bridges (hydrogen bonding and ionic bonding), cation-pi interactions, van der Waals forces and other bonds that are not covalent in nature.

Furthermore, said active agent(s) may be covalently attached to or to form ionic bond(s) with one or more linker group(s) L that is/are attached to the jasmine lactone or polymer of the invention, thus forming a conjugate of said active agent(s) and jasmine lactone or polymer of the invention.

The term “pendant group” as used herein, refers to a moiety that is attached to the backbone of the polymer. The term “side group” as used herein, refers to a moiety that is attached to the core molecule, e.g. a monomer. The terms “pendant group” and “side group” can mean the same thing or the specific definition given herein and should be understood as not limiting to one or another definition. E.g. in the case of poly(jasmine lactone) (PJL), the moiety forming the pendant group may be the (pent-2-en-1-yl)-group, attached at carbon number 5 in the below formula:

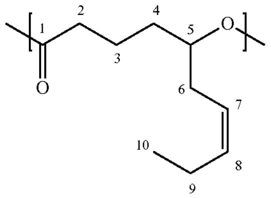

A side group of jasmine lactone (6-(pent-2-en-1-yl)tetrahydro-2H-pyran-2-one) refers to the (pent-2-en-1-yl)-group attached at carbon number 6 of tetrahydro-2H-pyran-2-one, according to the below formula:

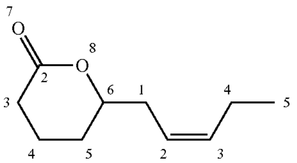

It is to be understood that the active agent may be directly connected to the polymer backbone or a monomer, the pendant group of the polymer or the side group of jasmine lactone, or part of a crosslink of the polymer, or there may be one or more successive moieties, e.g. linker groups L, in between the active agent and the polymer backbone or a monomer, the pendant group of the polymer or the side group of jasmine lactone, or crosslink of the polymer. The linker group L and/or the active agent corresponds to any of R1 and R2 of Formula [I] and Formula [III].

The terms “linker group L” or “linker” used herein and hereafter refer to chemical moieties that are attached to jasmine lactone or the polymers of the invention. Said linker group L may be neutral or positively or negatively charged. Furthermore, said linker group L may also be covalently attached to or form ionic bond(s) with an active agent, thus linking said active agent to said jasmine lactone or polymer of the invention. Said linker group L may also be covalently attached to or form ionic bond(s) with another linker group L. It is to be understood that a linker group L and a functional moiety can mean the same thing or the specific definition given herein and should be understood as not limiting to one or another definition. Examples of linker groups include, but are not limited to, a bond, —O—, —S—, —NH—, —(C═O)—, —O—(C═O)—, —(C═O)—O—, —NH(C═O)—, —(C═O)—NH—, —O—(C═O)—NH—, —NH—(C═O)—O—, —NH(C═O)—NH—, —(C═O)—S—, —S—(C═O)—, —S—(C═O)—NH—, —O—(C═O)—S—, —NH—(C═O)—S—, —O—(C═O)—$C_{1-10}$-alkylenyl-O—, —O—$C_{1-10}$-alkylenyl-(C═O)—O—, —O(C═O)—O—, —$C_{1-20}$-alkylenyl-$CO_2$—, —$C_{1-20}$-alkylenyl-O—, —$C_{1-20}$-alkylenyl-NH—, —$C_{1-20}$-alkylenyl-S—, —$C_{1-10}$-alkylenyl-N(O═CC═C)C═O, —$C_{1-10}$-alkylenyl-N(O═CC═C)C═O, —$(CH_2CH_2O)_mCH_2CH_2$—N(O═CC═C)C═O, —$C_{1-10}$-alkylenyl-S—S—$C_{1-10}$-alkylenyl-$CO_2$—, —$(CH_2CH_2O)_m$—$C_{1-10}$-alkylenyl-S—S—$C_{1-10}$-alkylenyl-$CO_2$—, —$C_{2-20}$-alkynyl, —O$(CH_2CH_2O)_m$—, —$(CH_2CH_2O)_m$—, —$(CH_2CH_2O)_nCH_2CH_2S$—, —$(CH_2CH_2O)_nCH_2CH_2N(R6)_2$, —$C_{1-20}$-alkylenyl-, optionally substituted with one or more halogen, $CO_2R6$, OR6, $N(R6)_2$, $N^+(R6)_3$, SR6, $C_{1-10}$-alkyl, $C_{2-10}$-alkenyl, $C_{1-10}$-haloalkyl, $C_{1-10}$-alkylenyl-$CO_2H$, $C_{1-10}$-alkylenyl-OH, $C_{1-10}$-alkylenyl-$N(R6)_2$, phenyl, wherein R6, R21, m, and n are as defined herein and hereafter, or salts thereof. It is to be understood that the linker group L can also, together with the carbon atoms that R1 and R2 of Formula [I] are attached to, form a saturated or partly unsaturated mono- or polycyclic cycloalkyl or heterocycle, or a mono- or polycyclic aryl or heteroaryl, optionally substituted with one or more substituents as defined herein and hereafter, or salts thereof. Specific examples of linker groups L include, but are not limited to, a bond, —S—, —NH—, —$NH_3^+$, —O—, —$SCH_2CH_2O$—, —$SCH_2CH_2NH$—, —$SCH_2CH_2NH_3^+$, —$SCH_2CH_2$—(C═O)—O—, —$SCH_2CH_2$—(C═O)—O—, —$OCH_2$—C(—OH)—$CH_2S$—, —O—(C═O)—$CH_2$—C(—SH)—(C═O)—O—, and —O—$(CH_2CH_2O)_3$—$CH_2CH_2$—S—.

Additional functional moieties that may be introduced to the polymers of the invention are those that change the properties of polymers, such as, but not limited to, mechanical properties, physical properties, chemical properties, thermal properties, electrical properties, optical properties, and degradation properties. Examples of these functional moieties include, but are not limited to, (adamantanylmethyl) amide and tert-butyldimethylsilanolate, and any derivatives thereof.

Alternatively, the linker group L is a stimuli sensitive linker (also called stimuli-responsive linker) that react in a response to including, but not limited to, changes in pH, light, temperature, magnetic field, sound, electric pulse, redox, or are sensitive to enzymes or glucose, and subsequently, release the active agent from the polymer. Examples of stimuli sensitive linkers include, but are not limited to, ester group, carbonate group, thioketal and disulfide (dithio) group.

The terms “modifying” and “modify” used herein and hereafter refers to introduction of functional moiety/moieties, e.g. linker group(s), or derivatives thereof, to a monomer or a polymer to form a modified monomer and a modified polymer, respectively. Therefore, it is to be understood that modifying a jasmine lactone or polymer of the invention forms a product that is referred herein and hereafter as a “modified” product. It is to be understood that at least a part of the monomers may be modified. An example of said monomer is, but not limited to, jasmine lactone monomer with Formula [III], and an example of said polymer is a polymer with Formula [I]. Further, said modified polymer includes both modified homopolymers and modified copolymers. Modifying said monomer or polymer is performed with a chemical reaction of a at least one suitable reagent, which may be a functional moiety or derivatives thereof, and the monomer or the polymer, or alternatively, said monomer or polymer is brought to close contact to at least one suitable reagent, which may be a functional moiety or derivatives thereof. Therefore, said functional moiety/moieties is/are covalently attached to the monomer or polymer, or form(s) ionic bond(s) to the monomer or the polymer. Modifying the jasmine lactone or the polymer of the invention may be performed before, during and/or after the polymerization reactions forming modified products.

It is to be understood that reacting or bringing to close contact a jasmine lactone or polymer of the invention with functional moiety/moieties, e.g. active agent(s), or derivatives thereof, forms a product that is referred herein and hereafter as a "functionalized" product. Therefore, said functional moiety/moieties is/are covalently attached to the monomer or polymer, or form(s) ionic bond(s) to the monomer or the polymer. Said formed functionalized product may be a functionalized jasmine lactone monomer and in the case of polymers, said product is generally referred as a composition. It is to be understood, that functionalized polymers and compositions can mean the same thing or the specific definition given herein and hereafter and should be understood as not limiting to one or another definition. It is also to be understood that the jasmine lactone monomers and the polymers may be modified jasmine lactone monomers and modified polymers. Therefore, said functionalized products may also be functionalized modified jasmine lactones and functionalized modified polymers (compositions) and thus, said active agents(s) is/are covalently attached to the linker group(s) of the modified monomer or modified polymer, or said active agent(s) form(s) ionic bond(s) to the linker groups(s) of the modified monomer or the modified polymer. Said introduction of active agent(s), or derivatives thereof, to jasmine lactones and polymers of the invention may be performed before, during and/or after the polymerization reactions forming functionalized products. It is to be understood that terms "modified" and "functionalized" can mean the same thing or the specific definition given herein and should be understood as not limiting to one or another definition.

It is to be understood that introduction of functional moiety also includes post-functionalization of the polymers and the jasmine lactones of the invention. In particular, the double bond of the jasmine lactone or the repeating unit of Formula [II] or other groups available on the polymer(s) can be reacted using various reactions types including, but not limited to, thiol-ene reaction, thiol-yne reaction, alkyne-azide reaction, Diels-Alder reaction, addition reaction, oxidation reaction, thiol-bromo click-reaction, esterification reaction, coupling reaction, amidation reaction, coordination polymerization, free-radical polymerization, atom transfer radical polymerization, and reversible addition-fragmentation chain transfer. It is to be understood that the introduction of functional moiety can comprise one or more successive reactions of the same or different reaction type.

The terms "polymerization reaction" and "polymerization" refers to reactions of monomers forming polymers. The terms "polymerization reaction" and "polymerization" can mean the same thing or the specific definition given herein and should be understood as not limiting to one or another definition. Polymerization reactions may use mechanisms of, including, but not limited to, cationic ring opening polymerization (ROP), anionic ROP, coordination-insertion ROP, activated monomer ROP, free-radical polymerization, atom transfer radical polymerization, and reversible addition-fragmentation chain transfer. Polymerization reactions include both step- and chain-growth polymerization. The polymerization reactions may be performed in the presence of or in the absence of an initiator. Examples of initiators include, but are not limited to, methoxy-poly(ethylene glycol, mPEG), propyl alcohol, glycerol, allyl alcohol, cetyl alcohol, bromobenzyl alcohol, mercaptobenzyl alcohol, cyanuric acid, chlorobenzyl alcohol, (2-methylbutyl)amine, polyoxyethylene bis(amine), ethylene diamine, and their derivatives. Catalyst such as organic, inorganic, metal catalyst may be used in the polymerization reactions. Examples of catalysts include, but are not limited to, tin-alkoxides, lanthanide alkoxides, thiourea cocatalysts, sulfonamide, phosphazene base, 1,8-diazabicyclo[5.4.0]undec-7-ene (DBU), 1,5,7-triazabicyclo-[4.4.0]dec-5-ene (TBD), methane- and trifluoromethanesulfonic acid, diphenyl phosphate (DPP), phosphoramidic acid, and rare earth metals and derivatives thereof.

It is to be understood that in a polymerization reaction of at least two different monomers to form a copolymer of the invention, all of the at least two different monomers may be present at the same time in the polymerization reaction. Alternatively, a first different monomer may be first present in the polymerization reaction and subsequently a second monomer, which is different from the first different monomer, will be added to the polymerization reaction, wherein the first different monomer is present. Further different monomers may be subjected to said polymerization reaction before, during or after the addition of said second monomer. For example, the jasmine lactone monomer may be polymerized in the presence of a modified jasmine lactone monomer to form a polymer of the invention. In another example, the jasmine lactone monomer may be first subjected to a polymerization reaction and during the polymerization reaction, a modified jasmine lactone monomer may be added to said polymerization reaction, thus forming a polymer of the invention. In a further example, a mixture of a jasmine lactone monomer, a modified jasmine lactone monomer and a lactide monomer may be subjected to a polymerization reaction to form a polymer of the invention. In yet another example, a mixture of the jasmine lactone monomer and a functionalized jasmine lactone is subjected to a first polymerization reaction to form a first polymer, and after said first polymerization reaction to form a first polymer, a mixture of a modified jasmine lactone monomer, lactide monomer and the said first polymer is subjected to a second polymerization reaction to form a second polymer.

It is to be understood that the structures of the polymers of the invention presented herein are only schematic presentations of the polymers. Therefore, it is to be understood that the linkers groups (L) and/or the active agents can be attached at one or more repeating unit of the polymer or jasmine lactone, at any possible atom. I.e. the following structure includes instances where the active agent (A) and/or the linker group (L) is/are attached to the repeating unit of the polymer and instances in which the active agent (A) and/or the linker group (L) is/are not attached to the repeating unit of the polymer:

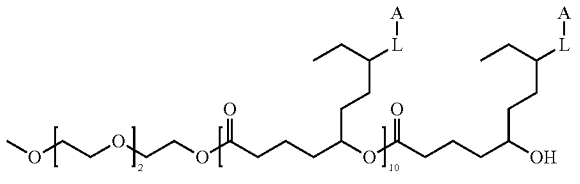

wherein L represents linker group(s), and A represents active agent(s), therefore, representing a polymer wherein all the repeating units contain an active agent (A) and/or a linker group (L) but is also representing a copolymer wherein none or a part of the repeating units, at any combinations, contain an active agent (A) and/or a linker group (L), the last-mentioned instance being exemplified by the following structure:

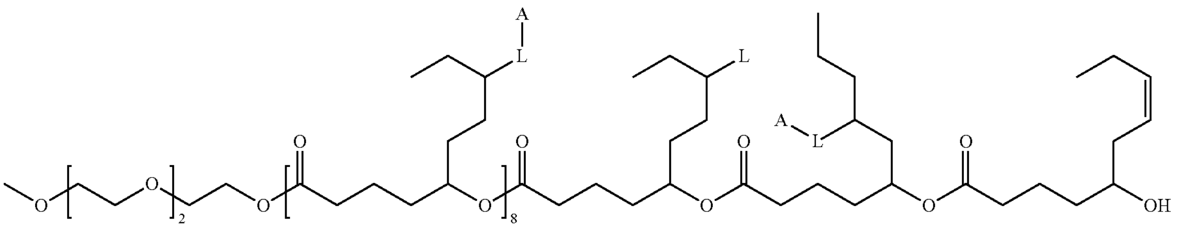

It is to be understood that the composition or the pharmaceutical composition of the present invention can consist of one or more combinations of different active agents and linker groups. Combinations of active agents include, but are not limited to, active pharmaceutical ingredient and unit having fluorescence (e.g. doxorubicin and fluorescein), active pharmaceutical ingredient and aptamer (e.g. trastuzumab and prostate specific antigen), active pharmaceutical ingredient, aptamer and unit having radioactivity (e.g. sorafenib, vascular endothelial growth factor and fludeoxyglucose). It is also to be understood that the two or more active agents can be present in the composition or the pharmaceutical composition of the present invention in different amounts.

The expression "pharmaceutically acceptable" represents being useful in the preparation a pharmaceutical composition that is generally safe, non-toxic, and neither biologically nor otherwise undesirable, and includes being useful for both veterinary use as well as human pharmaceutical use.

The term "salt" refers to salts that compounds of formula [I], [Ia], [Ib], [Ic], [Id], [Ie], [Iy], and [II] can form, the salts are known to be non-toxic or toxic and are commonly used to e.g. improve solubility of the polymer or composition. Typically, these are acid addition salts or base addition salts, as defined herein and hereafter, of the referred compounds. Examples of inorganic acids, that form suitable salts, include, but are not limited to, hydrogen chloride, hydrogen bromide, sulphuric, and phosphoric acids. Examples of organic acids, that form suitable salts, include, but are not limited to, acetic acid, lactic acid, malonic acid, succinic acid, and glutaric acid. Examples of base salts include, but are not limited to, those derived from inorganic bases such as aluminum, ammonium, calcium, potassium, sodium and zinc salts.

The term "pharmaceutically acceptable salt" refers to salts which are known to be non-toxic and are commonly used in the pharmaceutical literature. Typically, these are acid addition salts or base addition salts of the referred compounds of the invention.

The expression "acid addition salt" includes any non-toxic organic and inorganic acid addition salts that compounds of formula [I], [Ia], [Ib], [Ic], [Id], [Ie], [Iy], and [II] can form. Illustrative inorganic acids, which form suitable acid addition salts, include, but are not limited to, hydrogen chloride, hydrogen bromide, sulphuric and phosphoric acids. Illustrative organic acids, which form suitable acid addition salts, include, but are not limited to, acetic acid, lactic acid, malonic acid, succinic acid, glutaric acid, fumaric acid, malic acid, tartaric acid, citric acid, ascorbic acid, maleic acid, benzoic acid, phenylacetic acid, cinnamic acid, methane sulfonic acid, salicylic acid, and the like. The term "acid addition salt" as used herein also comprises solvates which the compounds and salts thereof are able to form, such as, for example, hydrates, alcoholates, and the like. These salts also include salts useful for the chiral resolution of racemates.

The expression "base addition salt" includes any non-toxic base addition salts that the compounds of formula [I], [Ia], [Ib], [Ic], [Id], [Ie], and [Iy] can form. Suitable base addition salts include, but are not limited to, those derived from inorganic bases such as aluminum, ammonium, calcium, copper, iron, lithium, magnesium, manganese, potassium, sodium, and zinc salts, in particular sodium and ammonium salts. Further examples of organic base addition salts include salts of trialkylamines, such as triethyl amine and trimethyl amine, and choline salts.

The terms "suitable reagent" and "reagent" refers to chemical compounds that react or do not react with another chemical compound. It should be understood that reagents are not limited to chemical compounds that are added to a system in order to bring about a reaction but also to chemical compounds (reactants) that, together with starting material (s) and other chemical compounds, form chemical compounds as product(s) that are distinct from the starting material(s). The reagents are consumed or are not consumed in reactions of polymers or jasmine lactones, or derivatives thereof. The terms "reagent" and "reactant" can mean the same thing or the specific definition given herein and should be understood as not limiting to one or another definition. Therefore, the term "reagent" refers to reagents, reactants, catalysts, active agents, active agents conjugates with linkers, intermediates, and organic and inorganic chemical compounds that form salts with the compounds of the invention. Examples of reagents include, but are not limited to, thiols, amines, 2-mercaptoethanol, 2,2-dimethoxy-2-phenylacetophenone, cysteamine hydrochloride, 3-mercaptopropionic acid, hydrogen chloride, acetic acid, triethylamine, doxorubicin, doxorubicin HCl, doxorubicin-TK, 3,3'-dithiodipropionic acid, N-(3-dimethylaminopropyl)-N'-ethylcarbodiimide (EDC), and 4-(dimethylamino)pyridine (DMAP).

The objects of the invention may be achieved by novel polymers comprising at least one repeating unit, wherein the at least one repeating unit has Formula [I]

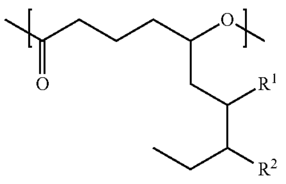

[I]

wherein each R1 and R2 is independently selected from a group consisting of H, R6, R21, SR6, SR21, SC(O)R6, SC(O)R21, OR6, OR21, OC(O)R6, OC(O)R21, OC(O)NHR6, OC(O)NHR21, NR6R21, $N(R6)_2$, NHC(O)R6, NHC(O)R21, NHC(O)NHR6, NHC(O)NHR21, $N^+(R6)_3$, $N_3$, $NO_2$, NOR6, CN, and halogen; or R1 and R2, together with the carbon atoms to which they are attached to, form a saturated or partly unsaturated mono-, bi-, tri- or tetracyclic cycloalkyl or heterocycle optionally substituted with one or more SR21, SR6, SC(O)R6, SC(O)R21, OR21, OR6, OC(O)R6, OC(O)R21, OC(O)NHR6, OC(O)NHR21, NR6R21, $N(R6)_2$, $N^+(R6)_3$, R6, R21, halogen, $N_3$, $NO_2$, NOR6, CN, $C_{1-10}$-alkyl, $C_{2-10}$-alkenyl, $C_{2-10}$-alkynyl, $C_{1-5}$-haloalkyl; a mono-, bi-, tri-, tetra- or pentacyclic aryl or heteroaryl optionally substituted with one or more SR21, SR6, SC(O)R6, SC(O)R21, OR21, OR6, OC(O)R6, OC(O)R21, OC(O)NHR6, OC(O)NHR21, NR6R21, $N(R6)_2$, $N^+(R6)_3$, R6, R21, halogen, $N_3$, $NO_2$, NOR6, CN, $C_{1-10}$-alkyl, $C_{2-10}$-alkenyl, $C_{2-10}$-alkynyl, $C_{1-5}$-haloalkyl;

R6 is each independently selected from a group consisting of H, $C_{1-20}$-alkyl, $C_{2-20}$-alkenyl, $C_{2-20}$-alkynyl, $C_{1-10}$-alkylenyl, $C_{1-10}$-haloalkyl, and phenyl;

R21 is each independently selected from $C_{1-10}$-alkylenyl-$CO_2H$, $C_{1-10}$-alkylenyl-OH, $C_{1-10}$-alkylenyl-NHR6, $C_{1-10}$-alkylenyl-SH, $C_{1-10}$-alkylenyl-N(O═CC═C)C═O, $C_{1-10}$-alkylenyl-S—$C_{1-10}$-alkylenyl-S—$C_{1-10}$-alkylenyl-N(O═CC═C)C═O, $(CH_2CH_2O)_m CH_2CH_2$—N(O═CC═C)C═O, $C_{1-10}$-alkylenyl-S—S—$C_{1-10}$-alkylenyl-$CO_2H$, $(CH_2CH_2O)_m$—$C_{1-10}$-alkylenyl-S—S—$C_{1-10}$-alkylenyl-$CO_2H$, $C_{2-20}$-alkynyl, $(CH_2CH_2O)_mH$, $(CH_2CH_2O)_nCH_2CH_2SH$, $(CH_2CH_2O)_nCH_2CH_2N(R6)_2$, $C_{1-10}$-alkylenyl, $C_{1-10}$-haloalkyl, optionally substituted with one or more halogen, $CO_2R6$, OR6, $N(R6)_2$, $N^+(R6)_3$, SR6, $N_3$, $NO_2$, NOR6, CN, $C_{1-10}$-alkyl, $C_{2-10}$-alkenyl, $C_{1-10}$-haloalkyl, $C_{1-10}$-alkylenyl-$CO_2H$, $C_{1-10}$-alkylenyl-OH, $C_{1-10}$-alkylenyl-$N(R6)_2$, phenyl;

m is an integer from 1 to 100;

n is an integer from 1 to 100;

or

R1 and R2 together form a double bond between the carbon atoms they are attached to, and with the proviso that R1 and R2 are not all hydrogen at the same time, or a salt thereof.

In one embodiment of the invention polymers comprise at least one repeating unit, wherein the at least one repeating unit has Formula [I], wherein R1 is H and R2 is SH, OH or $NH_2$, in particular SH. Polymers comprising at least one repeating unit, wherein the at least one repeating unit has Formula [I], wherein R1 is H and R2 is SH, OH or $NH_2$, in particular SH, are particularly versatile to modify with functional moiety/moieties.

In one embodiment of the invention polymers comprises at least one repeating unit, wherein the at least one repeating unit has Formula [I], wherein R1 is SH, OH or $NH_2$, in particular SH, and R2 is H.

In one embodiment of the invention polymers comprise at least one repeating unit, wherein the at least one repeating unit has Formula [I], wherein R1 and R2, together with the carbon atoms to which they are attached to, form a saturated or partly unsaturated mono-, bi-, tri- or tetracyclic cycloalkyl or heterocycle optionally substituted with one or more SR21, SR6, SC(O)R6, SC(O)R21, OR21, OR6, OC(O)R6, OC(O)R21, OC(O)NHR6, OC(O)NHR21, NR6R21, $N(R6)_2$, $N^+(R6)_3$, R6, R21, halogen, $N_3$, $NO_2$, NOR6, CN, $C_{1-10}$-alkyl, $C_{2-10}$-alkenyl, $C_{2-10}$-alkynyl, $C_{1-5}$-haloalkyl; a mono-, bi-, tri-, tetra- or pentacyclic aryl or heteroaryl optionally substituted with one or more SR21, SR6, SC(O)R6, SC(O)R21, OR21, OR6, OC(O)R6, OC(O)R21, OC(O)NHR6, OC(O)NHR21, NR6R21, $N(R6)_2$, $N^+(R6)_3$, R6, R21, halogen, $N_3$, $NO_2$, NOR6, CN, $C_{1-10}$-alkyl, $C_{2-10}$-alkenyl, $C_{2-10}$-alkynyl, $C_{1-5}$-haloalkyl;

R6, R21, m, and n are as previously defined;

or a salt thereof.

In one embodiment of the invention polymers comprise at least one repeating unit, wherein the at least one repeating unit has Formula [I], wherein R1 and R2 together form a double bond between the carbon atoms they are attached to. Polymers comprising at least one repeating unit, wherein the at least one repeating unit has Formula [I], wherein R1 and R2 together form a double bond between the carbon atoms they are attached to are particularly versatile to modify with functional moiety/moieties.

In one embodiment of the invention the polymers comprise at least one repeating unit, wherein the at least one repeating unit has Formula [I], wherein the polymer is a copolymer formed from monomers comprising lactones, carbonates, esters, lactams, alkenes, and epoxides.

In one preferred embodiment of the invention the polymers comprise at least one repeating unit, wherein the at least one repeating unit has Formula [I], wherein the polymer is a copolymer and other repeating unit(s) of the copolymer is/are formed from monomer(s) selected from the group consisting of lactones, preferably jasmine lactone; carbonates, esters, lactams, alkenes, epoxides, and any combination thereof.

In one preferred embodiment of the invention the polymers comprise at least one repeating unit, wherein the at least one repeating unit has Formula [I], wherein the polymer is a copolymer and other repeating unit(s) of the copolymer is/are formed from monomer(s) selected from the group consisting of jasmine lactone, lactide, glycolide, caprolactone, decalactone, butyrolactone, penta-decalactone, hydroxybutanoate, ethylene carbonate, ethylene, ethylene oxide, caprolactam, and any combination thereof.

In one more preferred embodiment of the invention the polymers comprise at least one repeating unit, wherein the at least one repeating unit has Formula [I], wherein the polymer is a copolymer and the other repeating unit of the copolymer is formed from monomer selected from lactide.

In one more preferred embodiment of the invention the polymers comprise at least one repeating unit, wherein the at least one repeating unit has Formula [I], wherein the polymer is a copolymer and the other repeating unit of the copolymer is formed from monomer selected from glycolide.

In one embodiment of the invention a polymer comprising at least one repeating unit, wherein the at least one repeating unit has Formula [I], is obtainable from reacting one or more monomer(s) selected from the group consisting of jasmine lactone, a modified jasmine lactone monomer with Formula (III) as described hereafter, carbonates, esters, lactams, alkenes, and any combination thereof, preferably selected from jasmine lactone, a modified jasmine lactone monomer with Formula (III) as described hereafter, lactide, glycolide, caprolactone, decalactone, butyrolactone, pentadecalactone, hydroxybutanoate, ethylene carbonate, ethylene, and caprolactam, optionally in the presence of an initiator and/or a catalyst, wherein the initiator, if present, is selected from the group consisting of methoxy-poly(ethylene glycol) (mPEG), poly (ethylene glycol) (PEG), propargyl alcohol, propyl alcohol, glycerol, allyl alcohol, cetyl alcohol, bromobenzyl alcohol, mercaptobenzyl alcohol, cyanuric acid, chlorobenzyl alcohol, (2-methylbutyl)amine, polyoxyethylene bis(amine), ethylene diamine, and their derivatives, preferably selected from mPEG, PEG, propargyl alcohol, and wherein the catalyst, if present, is selected from a group consisting of tin-alkoxides, lanthanide alkoxides, thiourea cocatalysts, sulfonamide, phosphazene base, 1,8-diazabicyclo[5.4.0]undec-7-ene (DBU), 1,5,7-triazabicyclo[4.4.0]dec-5-ene (TBD), methane- and trifluoro-methanesulfonic acid, diphenyl phosphate (DPP), phosphoramidic acid, lipases, hydrolases, and rare earth metals and derivatives thereof, preferably selected from TBD and DBU. It is to be understood that in the preparation of polymers of the invention, if end-groups of $OCH_2CH_2(OCH_2CH_2)_oOH$ or $OCH_2CH_2(OCH_2CH_2)_oOCH_3$ (o is an integer from 1 to 1000) are present in polymers of the invention then said end-groups derive from initiators such as mPEG or PEG used in the preparation of polymers of the invention. Therefore, it is to be understood that said end-groups are not formed from reacting monomers of ethylene oxide (epoxide) but from an initiator such as mPEG or PEG.

In one preferred embodiment of the invention the polymers comprise at least one repeating unit, wherein the at least one repeating unit has Formula [I], wherein the polymer is a copolymer formed from monomers that are selected from a group consisting of jasmine lactone, lactide, glycolide, caprolactone, decalactone, butyrolactone, pentadecalactone, hydroxybutanoate, ethylene carbonate, ethylene, ethylene oxide, and caprolactam. In a preferred embodiment the copolymer is formed from jasmine lactone and lactide. In another preferred embodiment the copolymer is formed from jasmine lactone and glycolide. In another yet preferred embodiment the copolymer is formed from jasmine lactone and a modified jasmine lactone monomer with Formula (III) as described hereafter, wherein R1 and R2 are as previously defined.

In one embodiment of the invention the polymers comprise at least one repeating unit, wherein the at least one repeating unit has Formula [I], wherein the polymer is a homopolymer.

In one embodiment of the invention the polymers comprise at least one repeating unit, wherein the at least one repeating unit has Formula [II]

[II]

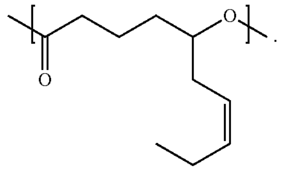

In still one embodiment of the invention the polymers comprise at least one repeating unit, wherein the polymer has a Formula that is selected from Formulas Ia to Ie

[Ia]

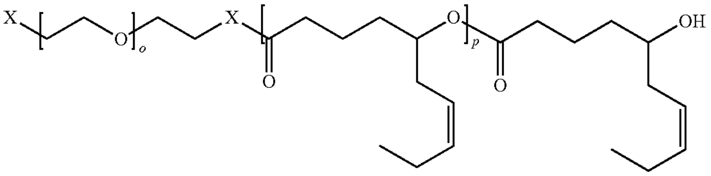

[Ib]

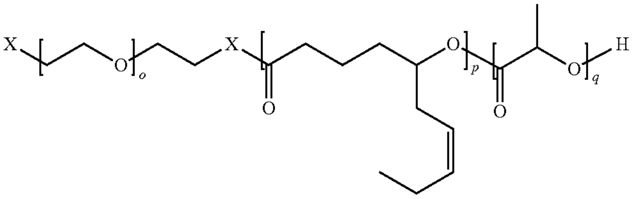

[Ic]

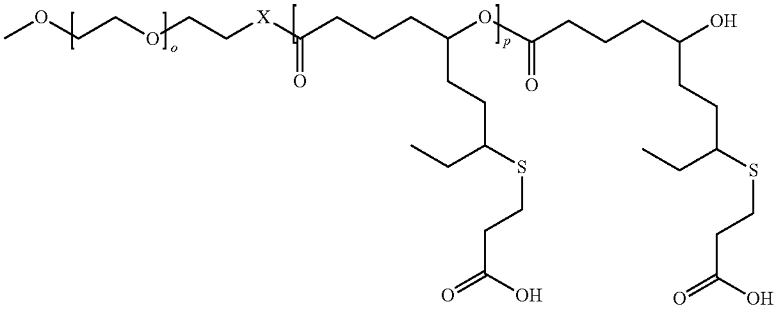

-continued

[Id]

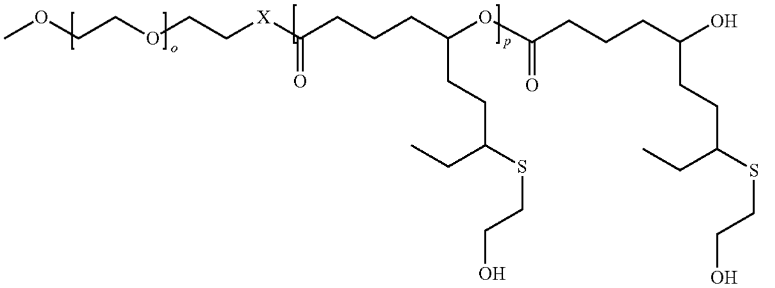

[Ie]

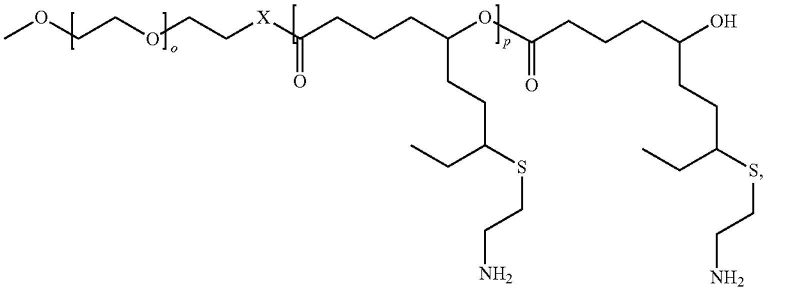

wherein each X is independently selected from a group consisting of O, OR6, S, SR6, and $N(R6)_2$, wherein R6 is each independently selected from a group consisting of H, $C_{1-20}$-alkyl, $C_{2-20}$-alkenyl, $C_{2-20}$-alkynyl, $C_{1-10}$-alkylenyl, $C_{1-10}$-haloalkyl, and phenyl;

o is an integer from 1 to 1000;

p is an integer from 10 to 2000;

q is an integer from 10 to 2000;

or a salt thereof. It is clear to a person skilled in the art that if X is attached to one carbon atom then X may be independently selected from a group consisting of OR6, SR6, and $N(R6)_2$, and if X is attached to two carbon atoms then X may be independently selected from a group consisting of O, and S.

In one embodiment of the invention the polymers comprise at least one repeating unit, wherein the at least one repeating unit has Formula [I], wherein the polymer has a Formula that is selected from Formulas If to Ij

[If]

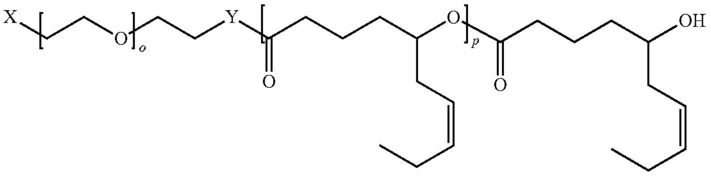

[Ig]

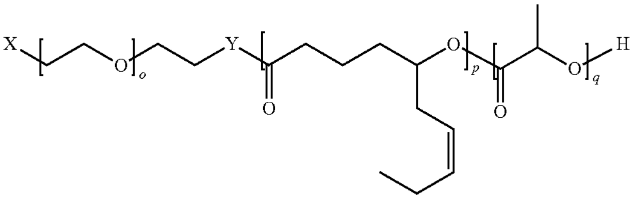

[Ih]

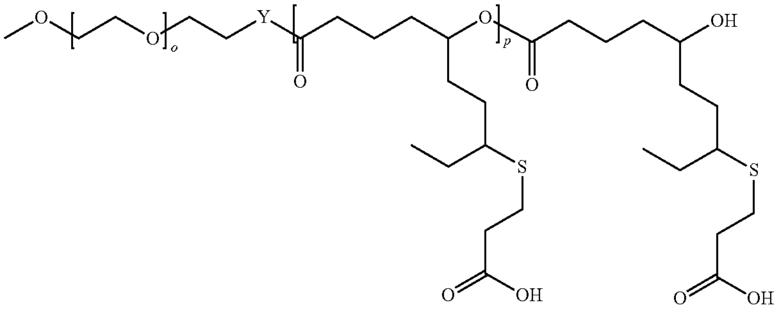

-continued

[Ii]

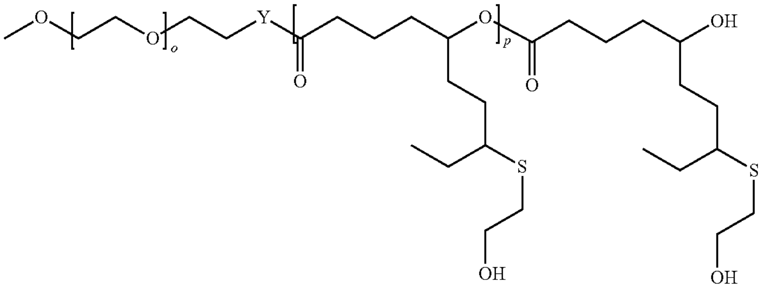

[Ij]

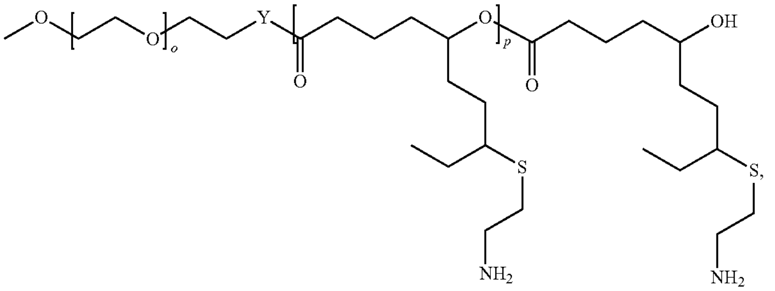

wherein each X is independently selected from a group consisting of OR6, SR6, and $N(R6)_2$, preferably selected from OR6, and SR6, more preferably selected from OR6;

each Y is independently selected from a group consisting of O, S, and NR6, preferably selected from O;

wherein R6 is each independently selected from a group consisting of H, $C_{1-20}$-alkyl, $C_{2-20}$-alkenyl, $C_{2-20}$-alkynyl, $C_{1-10}$-alkylenyl, $C_{1-10}$-haloalkyl, and phenyl, preferably selected from methyl;

is an integer from 1 to 1000;

p is an integer from 10 to 2000;

q is an integer from 10 to 2000;

or a salt thereof.

In one embodiment of the invention the polymers comprise at least one repeating unit, wherein the at least one repeating unit has Formula [I], wherein the polymer has Formula Ix

[Ix]

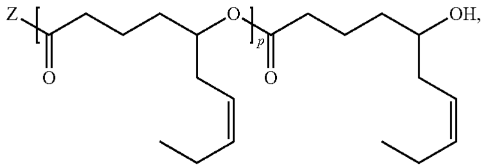

wherein

Z is independently selected from a group consisting of $OCH_2CH_2(OCH_2CH_2)_oOCH_3$, $OCH_2CH_2(OCH_2CH_2)_o$ OH, $OCH_2CH_2CH_3$, $OCH(CH_2OH)_2$, $OCH_2CH((OH)(CH_2OH))$, $OCHCH{=}CH_2$, $OCH_2C{\equiv}CH$, O—$C_{1-20}$-alkyl, O(2-BrPh), O(4-BrPh), O(2-ClPh), O(4-ClPh), O(2-SHPh), O(4-SHPh), (2-O, 4,6-di-OH(1,3,5-triazine)), $NH(CH_2(CH_3)(CH_2CH_2CH_3))$, $NHCH_2CH_2(OCH_2CH_2)_oNH_2$, $NHCH_2CH_2NH_2$, preferably selected from $OCH_2CH_2(OCH_2CH_2)_oOCH_3$, $OCH_2C{\equiv}CH$, and O—$C_{18}$-alkyl, more preferably selected from $OCH_2CH_2(OCH_2CH_2)_oOCH_3$;

is an integer from 1 to 1000;

p is an integer from 10 to 2000;

or a salt thereof.

In yet one embodiment of the invention the polymers comprise at least one repeating unit, wherein the polymer has a Formula Iy

[Iy]

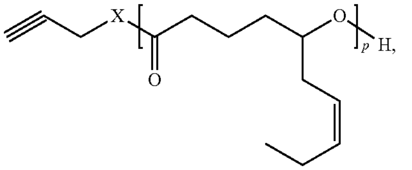

wherein each X is independently selected from a group consisting of O, S, and NR6, wherein R6 is each independently selected from a group consisting of H, $C_{1-20}$-alkyl, $C_{2-20}$-alkenyl, $C_{2-20}$-alkynyl, $C_{1-10}$-alkylenyl, $C_{1-10}$-haloalkyl, and phenyl;

p is an integer from 10 to 2000;

or a salt thereof.

The present invention also provides a novel composition comprising a polymer comprising at least one repeating unit, wherein the at least one repeating unit has Formula [I], and at least one active agent, or a salt thereof.

In one embodiment of the invention the composition comprises a polymer comprising at least one repeating unit, wherein the at least one repeating unit has Formula [I], wherein the at least one active agent(s), or derivatives thereof, is/are independently covalently attached to or form(s) ionic bond(s) with the polymer.

In one preferred embodiment of the invention the composition comprises a polymer comprising at least one repeating unit, wherein the at least one repeating unit has Formula

[I], wherein the at least one active agent(s) is/are independently selected from an active ingredient, an active pharmaceutical ingredient, an antibody, an aptamer, a unit having fluorescence, radioactivity or any other properties which can be detected, a protein, a peptide, and a flame retardant, and any derivatives thereof.

In yet one preferred embodiment the composition comprises a polymer comprising at least one repeating unit, wherein the at least one repeating unit has Formula [I], wherein the at least one active agent is an active pharmaceutical ingredient, or a derivative thereof.

In yet one preferred embodiment the composition comprises a polymer comprising at least one repeating unit, wherein the at least one repeating unit has Formula [I], wherein the at least one active agent is a unit having fluorescence, which can be detected, or a derivative thereof.

In yet one preferred embodiment the composition comprises a polymer comprising at least one repeating unit, wherein the at least one repeating unit has Formula [I], wherein the at least one active agent is a flame retardant, or a derivative thereof.

In one embodiment of the invention the composition comprises a polymer comprising at least one repeating unit, wherein the at least one repeating unit has Formula [I], wherein the at least one active agent(s) is/are independently selected from doxorubicin, daunorubicin, epirubicin, idarubicin, paclitaxel, docetaxel, cabazitaxel, camptothecin, cisplatin, fluorescein, fluorescein isothiocyanate (FITC), rhodamine, biotin, folic acid, transferrin, arginylglycylaspartic acid (RGD), rituximab, trastuzumab, cetuximab, bevacizumab, 2-carboxyethyl phenylphosphinic acid (CEPPA), phosphoric acid ($H_3PO_4$), phosphorous acid, 9,10-dihydro-9-oxa-10-phosphaphenanthrene-10-oxide, and fludeoxyglucose ($[^{18}F]FDG$), and any derivatives thereof.

In one preferred embodiment of the invention the composition comprises a polymer comprising at least one repeating unit, wherein the at least one repeating unit has Formula [I], wherein the at least one active agent is doxorubicin, or a derivative thereof.

In one preferred embodiment of the invention the composition comprises a polymer comprising at least one repeating unit, wherein the at least one repeating unit has Formula [I], wherein the active agents are doxorubicin and fludeoxyglucose ($[^{18}F]FDG$), or any derivatives thereof.

In yet one preferred embodiment of the invention the composition comprises a polymer comprising at least one repeating unit, wherein the at least one repeating unit has Formula [I], wherein the active agent is 2-carboxyethyl phenylphosphinic acid (CEPPA), or a derivative thereof.

The present invention also provides a method of producing polymer or a salt thereof, the method comprising the steps of i) providing jasmine lactone as a jasmine lactone monomer, ii) optionally modifying at least part of the jasmine lactone monomers of i) with at least one suitable reagent to form a modified jasmine lactone monomer with Formula (III),

[III]

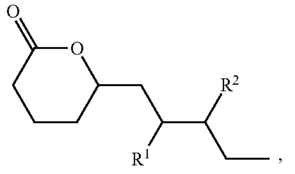

wherein R1 and R2 are as previously defined, iii) subjecting the jasmine lactone monomer of i) and/or the modified jasmine lactone monomer of ii) to a polymerization reaction to form a polymer.

In one embodiment of the invention is provided a method of producing a polymer, or a salt thereof, wherein the polymerization reaction of iii) is performed in the presence of at least one further monomer to form a copolymer.

In one embodiment of the invention is provided a method of producing a polymer, or a salt thereof, wherein the formed polymer or the formed copolymer is further reacted or brought to close contact with at least one suitable reagent capable of reacting or interacting with the formed polymer or the formed copolymer to form a modified polymer or a modified copolymer, respectively.

In one embodiment of the invention is provided a method of producing a polymer, or a salt thereof, wherein the formed polymer, the formed copolymer, the formed modified polymer or the formed modified copolymer is further reacted or brought to close contact with at least one active agent to form a composition.

In one embodiment of the invention is provided a method of producing a polymer, or a salt thereof, wherein at least a part of the jasmine lactone monomer of i) and/or the modified jasmine lactone monomer of ii) is reacted or brought to close contact with at least one active agent before or during the polymerization reaction of iii) to form a functionalized jasmine lactone and/or a functionalized modified jasmine lactone, respectively, and subjecting the formed functionalized jasmine lactone and/or the functionalized modified jasmine lactone to a polymerization reaction to form a composition.

In one embodiment of the invention is provided a method of producing a polymer, or a salt thereof, wherein the formed functionalized jasmine lactone and/or the functionalized modified jasmine lactone is subjected to a polymerization reaction in the presence of at least one further monomer to form a composition.

In one embodiment of the invention is provided a method of producing a polymer, or a salt thereof, wherein the at least one active agent(s) is/are independently selected from an active ingredient, an active pharmaceutical ingredient, an antibody, an aptamer, a unit having fluorescence, radioactive or any other properties which can be detected, a protein, a peptide, and a flame retardant, and any derivatives thereof.

In one embodiment of the invention is provided a method of producing a polymer, or a salt thereof, wherein the active agent comprises doxorubicin, daunorubicin, epirubicin, idarubicin, paclitaxel, docetaxel, cabazitaxel, camptothecin, cisplatin, fluorescein, fluorescein isothiocyanate (FITC), rhodamine, biotin, folic acid, transferrin, arginylglycylaspartic acid (RGD), rituximab, trastuzumab, cetuximab, bevacizumab, 2-carboxyethyl phenylphosphinic acid (CEPPA), phosphoric acid ($H_3PO_4$), phosphorous acid, 9,10-dihydro-9-oxa-10-phosphaphenanthrene-10-oxide, and fludeoxyglucose ($[^{18}F]FDG$), and any derivatives thereof.

Objects of the invention are also achieved by a novel pharmaceutical composition comprising one or more polymer as previously defined or an effective amount of one or more composition as previously defined, in combination with one or more other active ingredient(s), wherein the salt is a pharmaceutically acceptable salt.

In one preferred embodiment of the invention the pharmaceutical composition is together with one or more pharmaceutically acceptable excipient(s).

Objects of the invention are also achieved by a pharmaceutical composition as previously defined for use as a medicament.

UTILITY OF THE INVENTION

Polymers of the invention are polymers of jasmine lactone, which pendant groups of said polymers can readily be used for attaching functional moieties comprising active agents. Furthermore, discloses herein are modified jasmine lactones that can readily be used in methods of producing polymers of the present invention. Said modified jasmine lactones can be produced from jasmine lactone, which contains a 5-carbon side group, which can readily be used for attaching functional moieties including one or more active agent. Pharmaceutical compositions of polymers of jasmine lactone comprising one or more active agent may be useful in the treatment and prevention of a disease, disorder, or condition, in particular diseases, conditions, and conditions that include, but are not limited to, breast cancer, prostate carcinoma, ovarian cancer, uterine cancer, endometrial cancer, endometrial hyperplasia, lung cancer, colon cancer, tissue wounds, skin wrinkles and cataracts.

Further, compositions and pharmaceutical compositions of the present invention may be useful for the treatment of diseases and disorders described above and which may be prevented, treated, and/or ameliorated by said compositions and pharmaceutical compositions. Thus, the pharmaceutical compositions of the present invention may be used as a medicament. Further, the present invention includes methods of treating diseases or disorders as described herein of hereafter, comprising administering a pharmaceutical composition according to the claims to a patient or subject in need thereof. In addition, pharmaceutical composition of the present invention may be used for the manufacture of a medicament for use in treatment of diseases or disorders as described herein of hereafter.

The term “treatment or prevention” as used herein and hereafter includes prophylaxis, or prevention of, as well as lowering the individual’s risk of falling ill with the named disorder or condition, or alleviation, amelioration, elimination, or cure of the said disorder once it has been established.

The terms “administering” or “administered” to a subject or patient includes dispensing, delivering or applying the composition or pharmaceutical composition to the subject by any suitable route for delivery of the composition or pharmaceutical composition to a site in the body where desired.

Compositions and pharmaceutical compositions of the present invention may be administered in an effective amount within the dosage range of about 0.1 μg/kg to about 300 mg/kg, preferably between 1.0 μg/kg to 10 mg/kg body weight. Compounds of the present invention may be administered in a single daily dose, or the total daily dosage may be administered in divided doses of two, three or four times daily.

The term “effective amount” refers to an amount of a composition or a pharmaceutical composition that confers a therapeutic effect on the treated subject. The therapeutic effect may be objective (i.e. measurable by some test or marker) or subjective (i.e. subject gives an indication of or feels an effect). Such treatment need not necessarily completely ameliorate the condition of disease. Further, such treatment or prevention can be used in conjunction with other traditional treatments for reducing the condition known to those skilled in the art.

Compositions and pharmaceutical compositions of the invention are most preferably used alone or in combination i.e. administered simultaneously, separately or sequentially with other active ingredients, e.g. pharmaceutically active compounds or biologic products. The amounts of the composition(s) or pharmaceutical composition(s) of the invention, particularly a pharmaceutical composition comprising a polymer of Formula [I] and an active agent, or pharmaceutically acceptable salts thereof, and the other active ingredient(s) and the relative timings of administration will be selected in order to achieve the desired combined therapeutic effect. Compositions and pharmaceutical compositions of the invention may be administered by various routes, for example, parenteral, subcutaneous, intravenous, intraarticular, intrathecal, intramuscular, intraperitoneal, topical, and by intradermal injections, and via transdermal, rectal, buccal, oromucosal, nasal, ocular routes and via inhalation and via implant.

Compositions and pharmaceutical compositions may be formulated into a suitable pharmaceutical formulations; suitable administration forms include, for example, solutions, dispersions, suspensions, powders, capsules, tablets, pills, controlled release capsules, controlled release tablets and controlled release pills. In addition to the pharmacologically active ingredients, the pharmaceutical formulations of the compositions can contain suitable pharmaceutically acceptable carriers comprising excipients and auxiliaries that facilitate processing of the active agents into preparations that can be used pharmaceutically.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients.

Suitable pharmaceutically acceptable excipients include but are not limited to the following types of excipients: diluents (for example starches, mannitol), fillers (for example lactose, microcrystalline cellulose or calcium hydrogen phosphate), binders (for example pre-gelatised corn starch, polyvinylpyrrolidone or methylcellulose), additives (for example magnesium stearate, talc, silica), disintegrants (for example potato starch), lubricants (for example sodium lauryl sulphate), glidants (for example fumed silica, talc, magnesium carbonate), granulating agents (for example water, ethanol), coating agents (for example hydroxypropyl methylcellulose, gelatin, waxes, shellac, plastics, plant fibers), wetting agents (for example sorbitan monopalmitate, poloxamer 407), solvents (for example water), co-solvents (for example ethanol, propylene glycol), suspending agents (for example sorbitol, cellulose derivatives, edible hydrogenated fats), emulsifiers (for example lecithin or acacia), sweeteners (for example sucrose), flavoring agents (for example cherry, lime), flavor masking agents (for example vanilla, citrus), coloring agents (for example titanium oxide), anti-caking agents (for example silicon dioxide), humectants (for example glycerine, sorbitol), chelating agents (for example EDTA salts, histidine, aspartic acid), plasticizers (for example tributyl citrate, diethyl phthalate), viscosity increasing agents (for example methylcellulose), antioxidants (for example (ascorbic acid, cysteine), preservatives (for example methyl or propyl p-hydroxybenzoates, sorbic acid or ascorbic acid), stabilizers (for example polysorbate 20 & 80, poloxamer 407), surfactants (for example polyethylene glycol, polysorbate 80), and buffering agents (for example sodium and potassium phosphates, citrate, acetate, carbonate or glycine buffers depending on the targeted pH-range). The skilled artisan will appreciate that certain pharmaceutically acceptable excipients may serve more than one function and may serve alternative functions depending on how much of the excipient is present in the composition or pharmaceutical composition and what other ingredients are present in the composition.

The compositions and pharmaceutical compositions of the invention are prepared using techniques and methods known to those skilled in the art. Compositions and pharmaceutical compositions of the invention include, but are not limited to, for parenteral and topical administration that include, but are not limited to, sterile aqueous or non-aqueous solvents, suspensions and emulsions. Examples of non-aqueous solvents are propylene glycol, polyethylene glycol, vegetable oil, fish oil, and injectable organic esters. Aqueous carriers include, but are not limited to, water, water-alcohol solutions, including saline and buffered medial parenteral vehicles including sodium chloride solution, Ringer's dextrose solution, dextrose plus sodium chloride solution, Ringer's solution containing lactose, or fixed oils. Intravenous vehicles include, but are not limited to, fluid and nutrient replenishers, electrolyte replenishers, such as those based on Ringer's dextrose and the like. Aqueous compositions and aqueous pharmaceutical compositions according to the invention may comprise suitable buffer agents, such as sodium and potassium phosphates, citrate, acetate, carbonate or glycine buffers depending on the targeted pH-range. The use of sodium chloride as a tonicity adjuster is also useful. Compositions and pharmaceutical compositions may include other excipients, such as stabilizing agents or preservatives. Useful stabilizing excipients include surfactants (polysorbate 20 & 80, poloxamer 407), polymers (polyethylene glycols, povidones), carbohydrates (sucrose, mannitol, glucose, lactose), alcohols (sorbitol, glycerol propylene glycol, ethylene glycol), suitable proteins (albumin), suitable amino acids (glycine, glutamic acid), fatty acids (ethanolamine), antioxidants (ascorbic acid, cysteine etc.), chelating agents (EDTA salts, histidine, aspartic acid) or metal ions (Ca, Ni, Mg, Mn). Among useful preservative agents are benzyl alcohol, chlorbutanol, benzalkonium chloride and possibly parabens. The composition and pharmaceutical composition according to the present invention may be provided in concentrated form or in form of a powder to be reconstituted on demand. In such cases formulations of powder for solution for injection/infusion excipients mentioned above may be used. In case of lyophilizing, certain cryoprotectants are preferred, including polymers (povidones, poly-ethylene glycol, dextran), sugars (sucrose, glucose, lactose), amino acids (glycine, arginine, glutamic acid) and albumin. If solution for reconstitution is added to the packaging, it may consist e.g., of pure water for injection or sodium chloride solution or dextrose or glucose solutions.

Furthermore, polymers of formula [I] and [II] can be used as synthesis intermediates for the preparation of other compounds, in particular of other pharmaceutically active compositions, which are obtainable from polymers of formula [I] and [II] and, for example by introduction of substituents or modification of functional moieties.

Further, compositions and pharmaceutical compositions of the present invention that show reduced toxicities and/or enhanced efficacy of active agents may be useful in drug delivery and diagnosis. E.g., compositions and pharmaceutical compositions of the invention may be useful as drug deliver carriers as e.g. nanocarriers (NCs). The polymer-drug conjugates of the invention forming NCs show beneficial drug release and/or targeting properties, especially stimuli sensitive NCs offer improved drug release at the desired target site. Polymers comprising active pharmaceutical ingredient(s) and/or unit(s) that can be detected, e.g. units having fluorescence, may therefore be useful in drug diagnosis.

The polymers and compositions of the invention may also be useful in medical devices, cosmetic products, flame retardants, tissue engineering, coatings, paints, lubricants and biodegradable plastics.

EXAMPLES

Synthesis of Poly(Jasmine Lactone) Homopolymer (PJL, 1y')

1y'

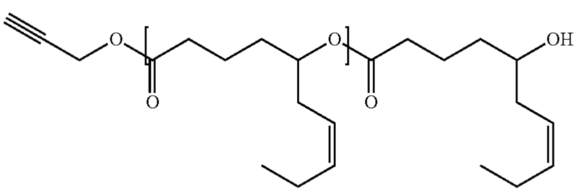

Poly(jasmine lactone) (PJL) was synthesized via ring opening polymerization (ROP) of jasmine lactone in bulk. The dried monomer jasmine lactone (5.00 g, 30.0 mmol) was transferred into a flask containing the initiating alcohol propargyl alcohol (0.07 g, 1.3 mmol) and stirred for 10-15 minutes to make a homogeneous mixture. 1,5,7-Triazabicyclo[4.4.0]dec-5-ene (TBD) (0.08 g, 0.6 mmol) was then added under a nitrogen atmosphere and the mixture was allowed to react for 11 h at room temperature. The obtained viscous liquid (91% conversion as per $^1$H NMR) was subsequently quenched by adding 5 mL of a solution of benzoic acid in acetone (0.03 g/mL), the polymer was precipitated in cold methanol and the residual solvent was evaporated under vacuum. Polymer PJL was recovered as colorless viscous liquid with 4.4 g yield.

FTIR: 2960 (C—H stretching), 1727 (C═O), 1157 (C—O, ester), 722 (C═C) $cm^{-1}$. $^1$H NMR (500 MHz, $CDCl_3$): $\delta_{ppm}$ 5.50-5.38 (m, 18H), 5.30-5.18 (m, 19H), 4.91-4.78 (m, 19H), 4.64 (d, J=2.4 Hz, 2H), 4.05-3.97 (m, 1H), 3.63-3.53 (m, 1H), 2.49-2.42 (m, 1H), 2.39-2.11 (m, 80H), 2.08-1.90 (m, 40H), 1.75-1.30 (m, 81H), 1.02-0.83 (m, 60H).

Synthesis of Boc-Protected Amine Terminated Homopolymer (PJL-NHBoc. 1ya')

1ya'

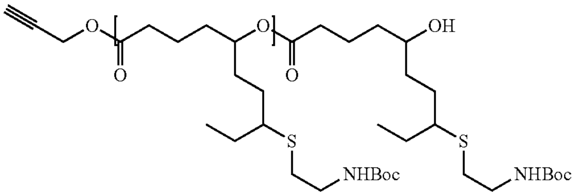

To prepare Boc-protected amine terminated polymer, PJL (1ya', 2 g, 0.65 mmol) and 2-(Boc-amino)ethanethiol (0.23 g, 1.3 mmol) were dissolved in DCM (5 mL). 2,2-Dimethoxy-2-phenylacetophenone (DMPA), 0.33 g, 13 mmol) was added to the mixture and the reaction mixture was stirred for 4 h in a UV cabinet fitted with a UV A/B bulb. The reaction mixture was precipitated in cold methanol and the solvent was removed under vacuum to yield Boc-protected amine terminated to homopolymer PJL-NHBoc (1x'). NMR analysis confirmed consumption of double bonds of PJL (1ya').

Synthesis of Poly(Jasmine Lactone) (PJL) Copolymer (mPEG-b-PJL. 1a')

1a'

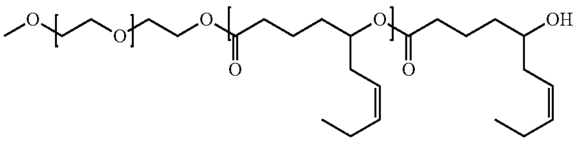

A di-block (AB type) copolymer of jasmine lactone was synthesized using methoxy-PEG (mPEG) as initiator. Dried mPEG (5.0 kDa, 5 g, 1.0 mmol) was added in a flask containing dry jasmine lactone (5.04 g, 30.0 mmol) and the mixture was heated to 50° C. and stirred for 10 minutes, until a homogeneous mixture was obtained. TBD (0.11 g, 0.8 mmol) was added and the mixture was allowed to react for 7 hours at 50° C. (88% conversion as per $^1$H NMR). The reaction mixture was then cooled, quenched by adding 5 mL of a solution of benzoic acid in acetone (0.3 g/5 mL) and the resulting polymer was precipitated in cold methanol followed by removal of residual solvent in vacuum. The obtained dry material was dissolved in a minimum quantity of acetone and re-precipitated in petroleum ether. Any residual solvent was evaporated under vacuum to yield the desired copolymer. The copolymer mPEG-b-PJL (1a') was recovered as wax-like material (8.2 g yield). FTIR: 2885 (C—H stretching), 1730 (C═O), 1341 (C—H bending), 1105 (C—O, ester and ether overlapped), 730 (C═C) cm$^{-1}$. $^1$H NMR (500 MHz, $CDCl_3$): $\delta_{ppm}$ 5.52-5.42 (m, 22H), 5.32-5.21 (m, 23H), 4.94-4.81 (m, 23H), 4.22 (dd, J=10.8, 5.9 Hz, 2H), 4.03 (s, 2H), 3.64 (s, 495H), 3.38 (s, 3H), 2.43-2.13 (m, 101H), 2.13-1.94 (m, 50H), 1.75-1.38 (m, 100H), 0.96 (dt, J=11.5, 5.0 Hz, 75H).

Post-Polymerization Modification of Copolymer (mPEG-b-PJL) to Insert Functional Moiety of Choice (mPEG-b-PJL-COOH, 1c')

1c'

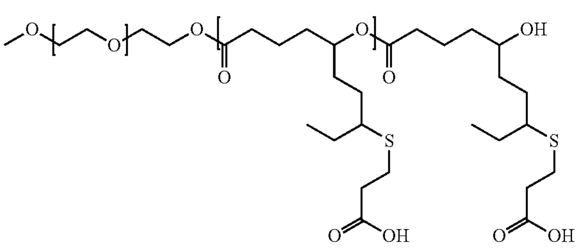

Thiol-ene click reaction was utilized to modify the available ene-groups of the mPEG-b-PJL chain. Briefly, mPEG-b-PJL (1a', 1.0 g, 0.11 mmol) and 3-mercaptopropionic acid (1.07 g, 10.1 mmol) were dissolved in DCM (5 mL). DMPA (0.097 g, 0.38 mmol) was added to the above mixture and stirred overnight in a UV cabinet fitted with a stirrer and UV A/B bulb. The reaction mixture was then precipitated in cold diethyl ether followed by removal of residual solvent in vacuum to recover the product as a white sticky solid (1.1 g yield).

FTIR: 2884 (C—H stretching), 1726 (C═O), 1342 (C—H bending), 1107 (C—O) cm$^{-1}$. $^1$H NMR (500 MHz, $CDCl_3$): $\delta_{ppm}$ 5.25-4.75 (m, 22H), 4.30-4.16 (m, 2H), 4.06 (s, 2H), 3.64 (s, 523H), 3.38 (s, 3H), 2.73 (d, J=6.5 Hz, 44H), 2.62 (t, J=6.9 Hz, 44H), 2.54 (s, 21H), 2.32 (s, 44H), 1.97-1.31 (m, 238H), 0.93 (ddd, J=22.6, 11.1, 6.3 Hz, 70H).

Post-Polymerization Modification of Copolymer (mPEG-b-PJL, 1a') to Insert Functional Moiety of Choice (mPEG-b-PJL-OH. 1d')

1d'

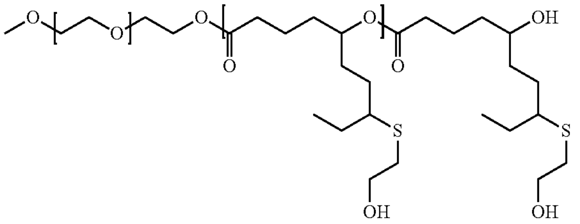

Thiol-ene click reaction was utilized to modify the available ene-groups of the mPEG-b-PJL chain. Briefly, mPEG-b-PJL (1a', 1.0 g, 0.11 mmol) and 2-mercaptoethanol (0.8 g, 10.1 mmol) was dissolved in DCM (5 mL). 2,2-Dimethoxy-2-phenylacetophenone (DMPA) (0.097 g, 0.38 mmol) was added to the above mixture and stirred overnight in a UV cabinet fitted with a stirrer and UV A/B bulb. The reaction mixture was then precipitated in cold diethyl ether followed by removal of residual solvent in vacuum to recover the product as a white sticky solid (1.1 g yield).

FTIR: 3433 (O—H), 2886 (C—H stretching), 1727 (C═O), 1341 (C—H bending), 1106 (C—O) cm$^{-1}$. $^1$H NMR (500 MHz, $CDCl_3$) $\delta_{ppm}$ 5.32-4.80 (m, 23H), 4.27-4.17 (m, 2H), 4.02 (d, J=29.8 Hz, 2H), 3.75-3.67 (m, 41H), 3.64 (s, 518H), 3.38 (s, 3H), 2.85-2.63 (m, 47H), 2.63-2.45 (m, 23H), 2.32 (s, 47H), 1.82-1.31 (m, 238H), 1.07-0.82 (m, 76H).

Post-Polymerization Modification of Copolymer (mPEG-b-PJL, 1a') to Insert Functional Moiety of Choice (mPEG-b-PJL-$NH_2$ HCl, 1e')

1e'

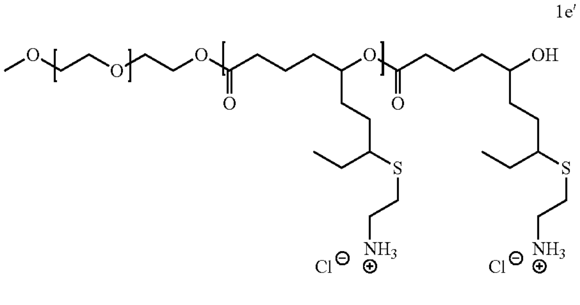

To prepare amine terminated polymer, mPEG-b-PJL (1a', 0.5 g, 0.06 mmol) and cysteamine hydrochloride (0.58 g, 5.1 mmol) was dissolved in ethanol (5 mL) containing one mL of DCM. DMPA (0.05 g, 0.2 mmol) and stirred overnight in UV cabinet fitted with a stirrer and UV A/B bulb. The reaction mixture was filtered, and the solvent of the filtrate was removed under vacuum. The dried product was dissolved in water and dialyzed (molecular weight cut off (MWCO): 2 kDa) for 4 days against water and freeze dried to obtain the purified product as a light yellow colored solid (0.52 g yield).

FTIR: 2877 (C—H stretching), 1727 (C═O), 1342 (C—H bending), 1107 (C—O) $cm^{-1}$. $^1H$ NMR (500 MHz, DMSO-$d_6$): $\delta_{ppm}$ 5.42 (s, 7H), 5.27 (d, J=36.6 Hz, 7H), 5.07-4.58 (m, 15H), 3.49 (s, 495H), 3.22 (d, J=3.5 Hz, 3H), 2.89 (d, J=6.8 Hz, 32H), 2.72-2.56 (m, 31H), 2.35-2.05 (m, 58H), 1.90 (s, 14H), 1.71-1.19 (m, 159H), 1.04-0.60 (m, 70H).

Conjugation of Ddoxorubicin (DOX) to mPEG-b-PJL-OH (1d') via Disulfide Linkage (mPEG-b-PJL-S-S-DOX, 1dx')

Subsequently, doxorubicin HCl (DOX, 0.1 g, 0.18 mmol), DTPA (0.04 g, 0.22 mmol) and triethylamine (0.08 mL, 0.54 mmol) were dissolved in DMF (10 mL), stirred for 24 h in dark and the reaction was monitored by Thin-layer chromatography (TLC). After completion of reaction, the mixture was cooled to 0° C. and N-(3-dimethylaminopropyl)-N'-ethylcarbodiimide (EDC, 0.14 g, 0.9 mmol) was added to the reaction mixture and the reaction mixture was stirred for 1 h. A solution of mPEG-b-PJL-OH (1d', 0.16 g, 0.018 mmol) and 4-(dimethylamino)pyridine (DMAP, 0.01 g, 0.09 mmol) in DMF (5 mL) was added to the above reaction mixture. The reaction mixture was stirred for 2 days at room temperature and then dialyzed against water for one week to remove unreacted DOX, DTPA, EDC, and DMAP. The purified solution was freeze dried to obtain a dark red solid as the product mPEG-b-PJL-S-S-DOX (1dx', 0.22 g yield).

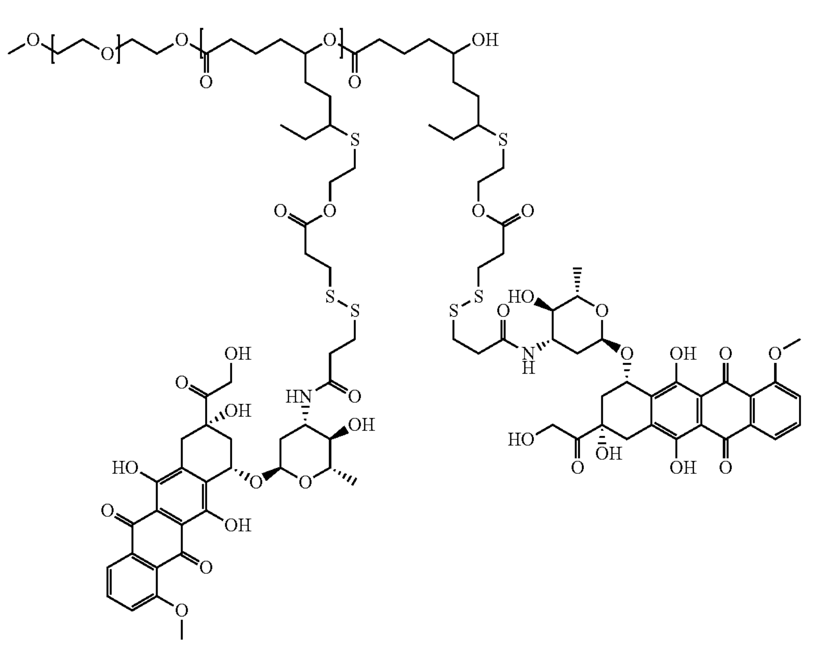

1dx'

Carbodiimide coupling reaction was utilized to conjugate doxorubicin to the pendant group of the polymer. A reduction sensitive linker (3,3'-dithiodipropionic acid) was utilized to synthesize polymer-drug conjugate in order to achieve site-specific controlled drug release. The disulfide linker was first converted into its anhydride form using reported procedure. Briefly, 3,3'-dithiodipropionic acid (3.0 g, 48 mmol) was dissolved in acetyl chloride (30 mL) and the reaction mixture was refluxed for 12 h at 70° C. The solvent was removed under vacuum and the residue was washed with ethyl ether and vacuum-dried to afford the anhydride to form of dithiodipropionic acid (DTPA, 2.6 g) as a white solid. FTIR: 1793 (C═O, anhydride), 1043 (CO—O—CO) $cm^{-1}$.

Synthesis of Thioketal Linker (TK, Reactive Oxygen Species Responsive Linker, 1z')

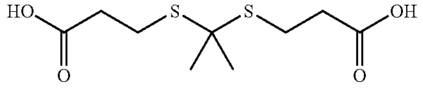

Anhydrous acetone (5.8 g, 98.2 mmol) and anhydrous 3-mercaptopropionic acid (5.2 g, 49.1 mmol) were mixed with dry hydrogen chloride and stirred for 6 h at room temperature. The reaction mixture was then placed on an ice-salt mixture and to achieve crystallization. The crystallized product was then washed several times with cold hexane and ice cold water. The white colored product was then dried in vacuum to acquire TK (1z', 3.6 g yield).

NMR (400 MHz, $CDCl_3$): $\delta_{ppm}$ 2.91 (4H), 2.68 (4H), 1.60 (6H).

Synthesis of Doxorubicin-TK (DOX-TK, 1zx')

1zx'

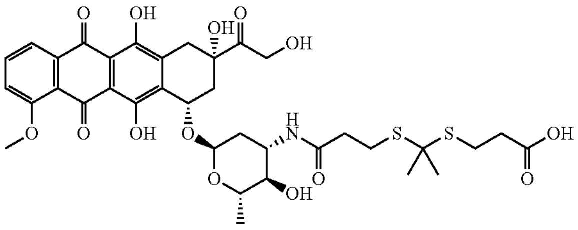

Coupling of drugs to the TK linker was performed via carbodiimide coupling. Briefly, TK (1z', 0.07 g, 0.28 mmol), N-(3-dimethylaminopropyl)-N'-ethylcarbodiimide (EDC, 0.064 g, 0.33 mmol) and N-hydroxysuccinimide (0.038 g, 0.33 mmol) were dissolved in DCM (10 mL), and the mixture was cooled to 0° C. and stirred for 1 h. Doxorubicin HCl (DOX, 0.15 g, 0.28 mmol) was dissolved separately in DCM (10 mL) containing 100 μL of triethylamine and added to the above mixture. The reaction mixture was then stirred for 24 h in dark and the reaction was monitored by TLC. After completion of reaction, the reaction mixture was filtered and solvent was evaporated to afford DOX-TK (1zx').

Synthesis of Docetaxel-TK (DTX-TK, 1zy')

1zy'

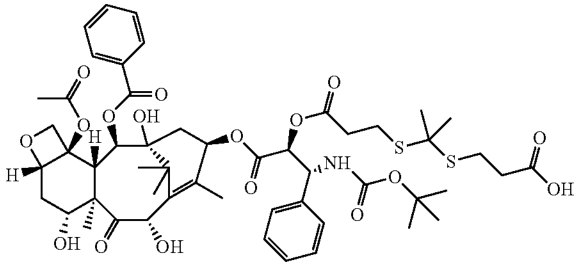

To prepare DTX-TK, TK (1z', 0.047 g, 0.18 mmol) and N-(3-dimethyl-aminopropyl)-N'-ethylcarbodiimide (EDC, 0.069 g, 0.36 mmol) were dissolved in DCM (10 mL), and the mixture was cooled to 0° C. and stirred for 30 min. Docetaxel (DTX, 0.15 g, 0.18 mmol) and DMAP (0.044 g, 0.36 mmol) was dissolved separately in DCM and added to the above mixture, stirred in dark for 36 h and the reaction was monitored by TLC. After completion of reaction, the reaction mixture was filtered and solvent was evaporated to afford DTX-TK (1zy').

Conjugation of Doxorubicin (DOX) and Docetaxel (DTX) to mPEG-b-PJL-OH (1d') using DOX-TK (1zx') and DTX-TK (1zy') to synthesize mPEG-b-PJL-TK-DOXDTX (1dxy')

1dxy'

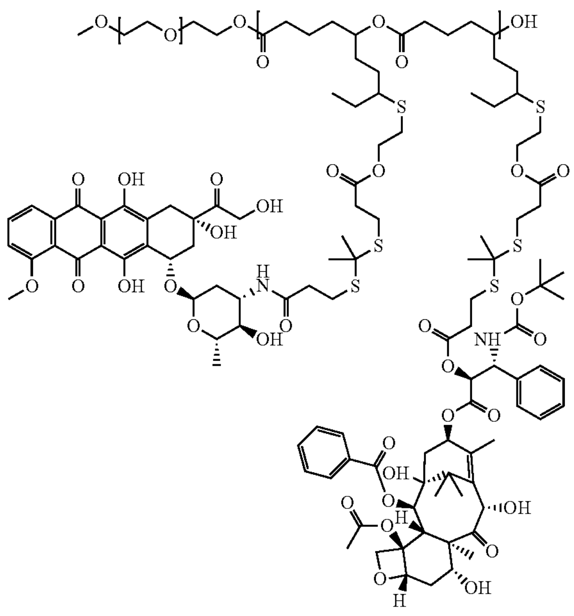

To a solution of intermediates DOX-TK (1zx') and DTX-TK (1zy') in DMF (10 mL) was added EDC (0.04 g, 0.2 mmol) at 0° C. and the reaction mixture was stirred for 30 min. A solution of mPEG-b-PJL-OH (1d', 0.5 g, 0.056 mmol) and DMAP (0.007 g, 0.056 mmol) in DMF (10 mL) was added to the reaction mixture and the reaction mixture was stirred for 40 h at room temperature while monitored by TLC. After reaction completion, the mixture was transferred to a dialysis tubing and dialyzed against water for two weeks to remove reactants and reagents. The purified solution was freeze dried to obtained ROS responsive polymer drug conjugate mPEG-b-PJL-TK-DOXDTX (1dxy') (0.68 g).

Drug Content:

The amount of DOX presented in polymer conjugate was determined using UV-Vis spectroscopy. mPEG-b-PJL-S-S-DOX (1dx', 1 mg) was dissolved in 1 mL of phosphate buffer saline (PBS) and the absorption at λmax 481 nm was recorded using NanoDrop 2000c spectrophotometer (Thermo Fisher Scientific, USA). The drug concentration was calculated using pre-prepared standard calibration curve and it was found that each mg of conjugate contains about 0.3 mg of DOX. FIG. 1 represent the overlapped UV-Vis spectra of DOX and its polymer conjugate mPEG-b-PJL-S-S-DOX (1dx').

Figure 2:
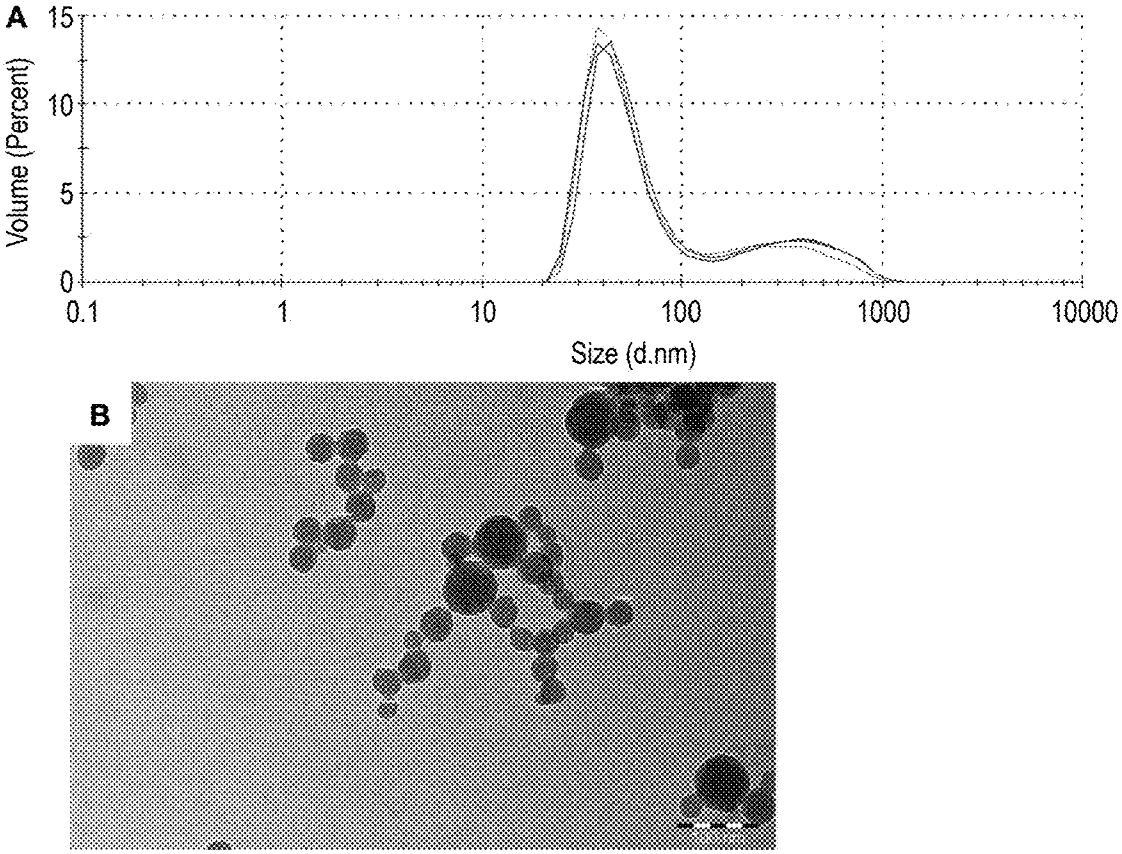
FIG. 2*a* illustrates an example of size distribution by volume (volume (%) vs size (d. nm)) of DOX conjugate mPEG-b-PJL-S-S-DOX (1dx') from a size distribution measurement using dynamic light scattering (DLS)
FIG. 2*b* an example of a Transmission Electron Microscopy (TEM) image of a drug-polymer conjugate (mPEG-b-PJL-S-S-DOX, 1dx') after re-dispersion of said conjugate in water.

Size of Drug-Polymer-Conjugates:

The size and polydispersity index of DOX conjugate mPEG-b-PJL-S-S-DOX (1dx') was measured by dynamic light scattering (DLS) using a ZetaSizer NanoZS® (Malvern Instruments, UK). Samples were diluted (50 μg/mL with respect to polymer) with MilliQ water and transferred into cuvettes for analysis. Measurements were performed at 25° C. and data analysis was carried out using the Malvern ZetaSizer software version 7.12. FIG. 2*a* represents size distribution by volume (volume (%) vs size (d. nm)) of DOX conjugate mPEG-b-PJL-S-S-DOX (1dx') from a size distribution measurement using DLS. Transmission Electron Microscopy (TEM) images were taken to confirm the size and to determine the surface morphology. Sample (50 μg/mL) was imaged on TEM grids without staining. TEM images were taken using a JEM 1400-Plus (JEOL Ltd., Tokyo, Japan). To perform the TEM observations, a drop of the diluted sample was directly deposited on the copper grid and observed in TEM after drying. FIG. 2*b* represents an example of a TEM-image of a drug-polymer conjugate (mPEG-b-PJL-S-S-DOX, 1dx') after redispersion of said conjugate in water.

Figure 3:
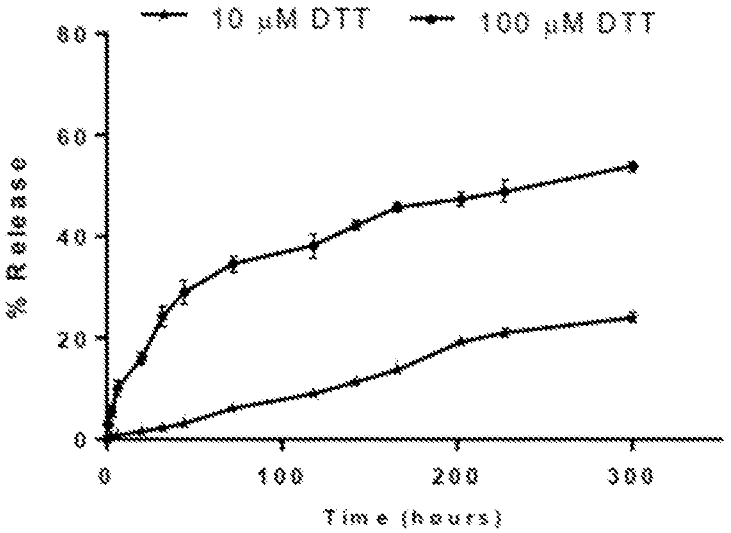
FIG. 3 illustrates the in-vitro release (in %) of DOX from conjugate mPEG-b-PJL-S-S-DOX (1dx') vs time (h) using 10 μM DTT (★) or 100 μM DTT (●) at pH 5.0. Release was performed in the presence of dithiothreitol (DTT) in order to initiate the cleavage of the disulfide bond present in the conjugate mPEG-b-PJL-S-S-DOX (1dx') structure. The experiment indicates that at higher DTT concentration more drug release can be obtained providing a stimuli responsive drug release of DOX from conjugate mPEG-b-PJL-S-S-DOX (1dx').

In-Vitro Drug Release:

The release profile of DOX from conjugate mPEG-b-PJL-S-S-DOX (1dx') was determined by a dialysis method at pH 5.0 in the presence of different quantity of dithiothreitol (DTT). Briefly, a calculated quantity of mPEG-b-PJL-S-S-DOX (1dx', 5 mg) was dissolved in release media i.e. acetate buffer (pH 5.0 containing either 10 μM or 100 μM of DTT). The solution was then placed in dialysis tubing (Float-A-Lyzer) having the molecular weight cut off (mwco) of 3.5-5 kDa. The samples were dialysed against 500 mL of release media at 37° C. The release media was replaced with fresh release media every 24 h. The volume of solution in the dialysis tubing was measured at appropriate time intervals (~6 h), and restored to the original with release media, if necessary. Samples (5 μL) were withdrawn directly from the dialysis tubing at predetermined time intervals and the volume of solution in the dialysis tubing was restored with fresh release media. Samples were analysed using a UV-Vis spectrophotometer at λmax 492 nm to calculate the amount of DOX remaining in the dialysis bag. FIG. 3 represents results from a release profile determination of DOX from conjugate mPEG-b-PJL-S-S-DOX (1dx').

In-Vitro Cell Studies:

Triple negative breast cancer cells MDAMB-231, and healthy cells of mouse embryonic fibroblasts (MEF) (ATCC) were used for in vitro studies. The cells were cultured in high-glucose Dulbecco's Modified Eagle Medium (DMEM) supplemented with 10% fetal bovine serum (FBS), 1% penicillin-streptomycin and 2 mM L-glutamine at 37° C., in a humidified incubator with 5% $CO_2$. Cells were passaged 2-3 times a week once they reached 90-100% confluency.

Figure 4:
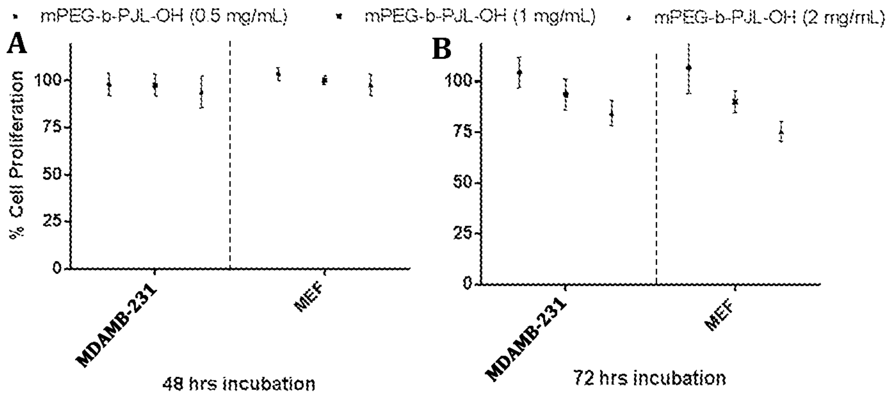
FIG. 4 illustrates an example of in-vitro toxicity profiles of a mPEG-b-PJL-OH polymer (1d') on normal (Mouse Embryonic Fibroblasts, MEF) and a cancer (MDAMB-231) cell lines, after 48 hours (FIG. 4A); and 72 hours (FIG. 4B) of incubation of said cell lines (% cell proliferation vs MEF and MDAMB-231 cell lines using said incubation times of 48 h and 72 h and different concentrations of mPEG-b-PJL-OH polymer (1d'); 0.5 mg/mL (●); 1 mg/mL (■); and 2 mg/mL (▲)). Results indicates that polymer samples with concentration of 0.5 mg/mL do not initiate toxicity at the time points.
Figure 5:
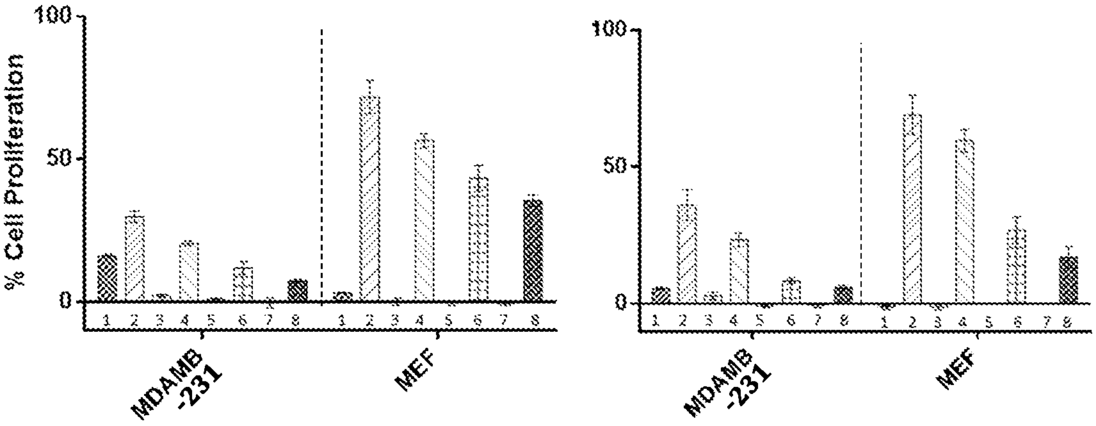
FIG. 5 illustrates an example of percentage proliferation observed of cancer (MDAMB-231) and normal (MEF) cell lines after incubation with different concentrations of doxorubicin HCl (DOX: 25 μg/mL (1); 50 μg/mL (3); 100 μg/mL (5); and 150 μg/mL (7)) or DOX-conjugate mPEG-b-PJL-S-S-DOX (1dx', DOX-PJL) containing different amounts of conjugated DOX: 25 μg/mL (2); 50 μg/mL (4); 100 μg/mL (6); and 150 μg/mL (8)) of said cell lines for 24 hours (FIG. 5*a*); and 72 hours (FIG. 5*b*). Results clearly indicates that conjugate mPEG-b-PJL-S-S-DOX (DOX-PJL, 1dx') differentiate between normal and cancer cells and thus low toxicity was observed with MEF cells whereas free DOX was found to be equally cytotoxic regardless the cell line used.

A WST-1 cell viability assay was used to determine cytotoxicity of polymer and DOX efficacy in cancerous and healthy cells. MDAMB-231 and MEF cells were incubated overnight in a 96-well-plate (7000 cells per well) in cell growth media at 37° C. with 5% $CO_2$. The following day, the cell growth media were replaced with fresh media containing different concentrations of mPEG-b-PJL-OH polymer (1d'; 0.5, 1.0, or 2.0 mg/mL), DOX HCl (25, 50, 100, or 150 μg/mL) or DOX-PJL conjugate mPEG-b-PJL-S-S-DOX (1dx'; 25, 50, 100, or 150 μg/mL) and incubated for 48 h or 72 h. Sample stocks were prepared in PBS and all the dilutions for the cell viability assay were prepared in cell growth media. After 48 h and 72 h incubation at 37° C., 5% $CO_2$, 10 μL of WST-1 cell proliferation reagent was added and the plate was incubated for additionally 2 h. The absorbance of samples was then read according to the manufacturer protocol (420-480 nm). The percentage cell proliferation was reported relative to untreated cells (100% viability). To eliminate the background due to doxorubicin, doxorubicin controls without cells were prepared and absorbance values were measured and subtracted prior to the plotting. FIGS. 4A and 4B represents results from the in-vitro toxicity profiles of a mPEG-b-PJL-OH polymer (1d') on the MEF and MDAMB-231 cell lines. FIGS. 5B and 5B represents results from the in-vitro toxicity profiles of DOX and mPEG-b-PJL-S-S-DOX (DOX-PJL, (1dx')) on the MEF and MDAMB-231 cell lines.

Figure 6:
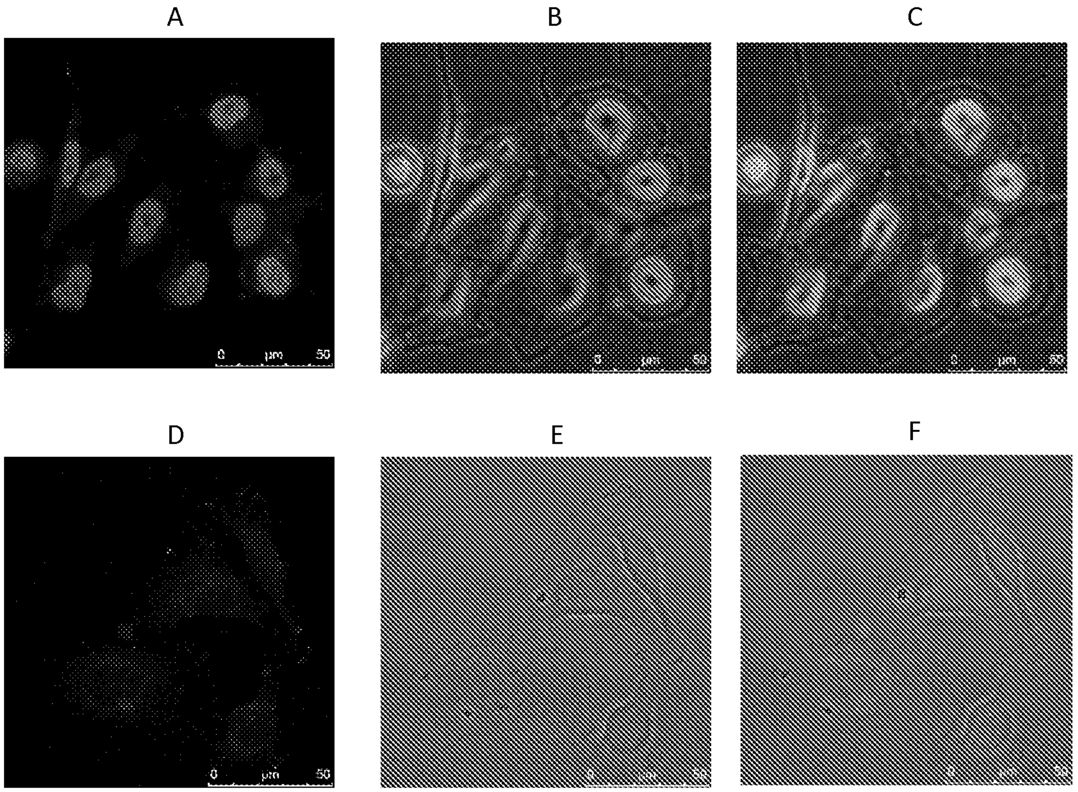
FIG. 6 illustrates an example of confocal images showing cellular uptake of doxorubicin (DOX) and conjugate PJL-DOX (mPEG-b-PJL-S-S-DOX, 1dx') in MDAMB-231 cells after 30 min incubation: DOX in MDAMB-231 cells (FIG. A); MDAMB-231 cells (FIG. B); merged image of (A) and (B) (FIG. C); PJL-DOX (mPEG-b-PJL-S-S-DOX, 1dx') in MDAMB-231 cells (FIG. D); MDAMB-231 cells (FIG. E); merged image of (D) and (E) (FIG. F). Conjugated DOX (mPEG-b-PJL-S-S-DOX (1dx')) is less fluorescent than free drug as shown in FIG. 7.
Figure 7:
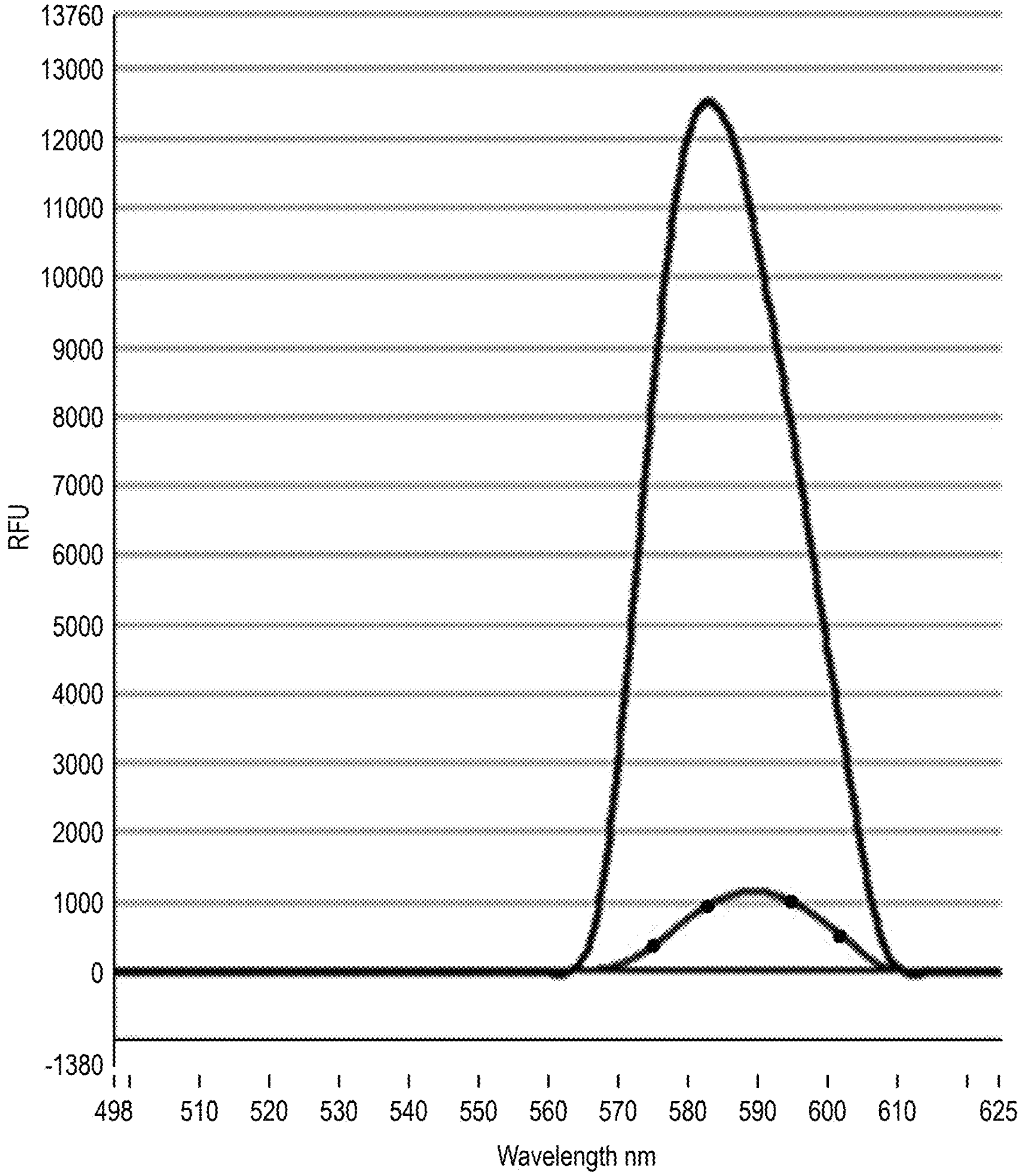
FIG. 7 illustrates an example of a fluorescence spectra of free DOX (—) and DOX conjugated with polymer (mPEG-b-PJL-S-S-DOX (1dx'), (●)) (wavelength (nm) vs relative fluorescence units (RFU)). Conjugated DOX (mPEG-b-PJL-S-S-DOX (1dx')) is less fluorescent than DOX.
Figure 8:
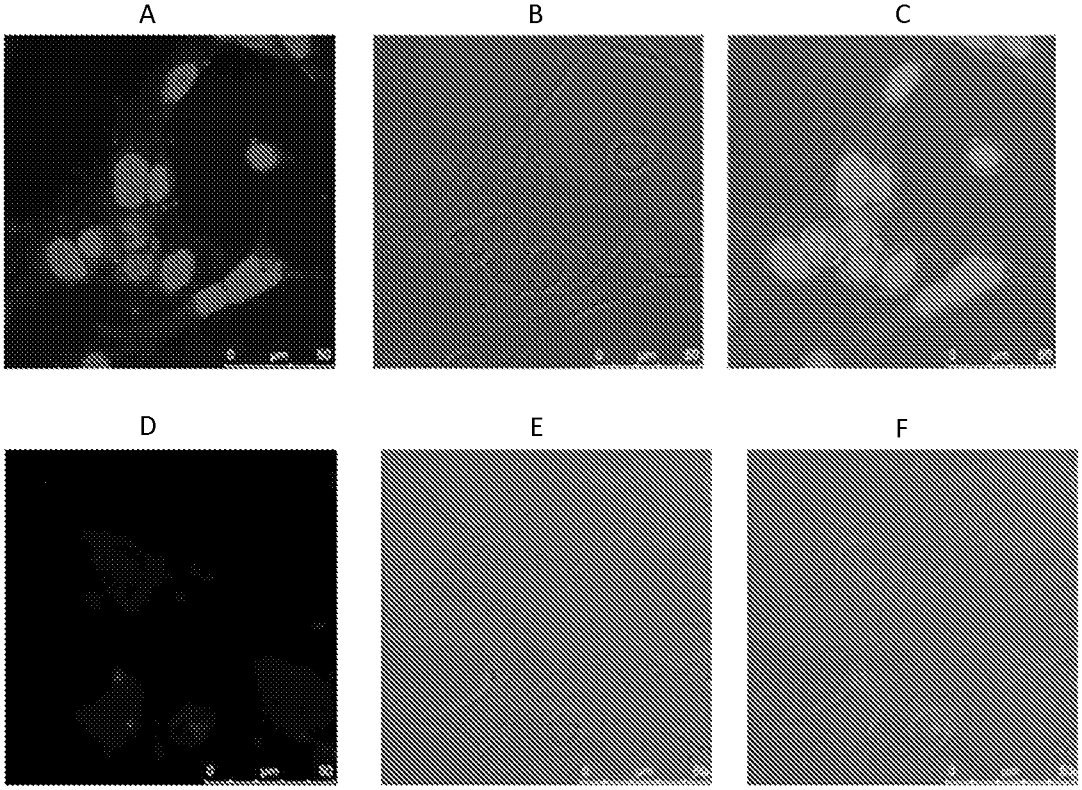
FIG. 8 illustrates an example of confocal images showing cellular uptake of DOX and its conjugate PJL-DOX (mPEG-b-PJL-S-S-DOX (1dx')) in normal MEF cells: DOX in MEF cells (FIG. A); MEF cells (FIG. B); merged image of (A) and (B) (FIG. C); PJL-DOX (mPEG-b-PJL-S-S-DOX (1dx')) in MEF cells (FIG. D); MEF cells (FIG. E); merged image of (D) and (E) (FIG. F). Conjugated DOX (mPEG-b-PJL-S-S-DOX (1dx')) is less fluorescent than free drug as well as with conjugated DOX (mPEG-b-PJL-S-S-DOX (1dx')) fluorescence observed with MDAMB-231 cells. These results indicate minimum cleavage of disulfide bond of mPEG-b-PJL-S-S-DOX (1dx')) in normal cells due to inadequate availability of glutathione. This in turn produced less toxicity to the normal cells compared to the cancer cells.

Cellular Uptake (by Confocal Microscopy):

Cellular uptake was evaluated by fixed cell confocal imaging at 0.5 h time point. The microscopy setup consisted of Leica TCS SP5 STED (Leica Microsystems), LASAF software (Leica application suite), photo multiplier tube (PMT) and 100× oil objectives. The imaging was performed using sequential scanning option consisting of single-photon excitation for free DOX and DOX conjugate mPEG-b-PJL-S-S-DOX (1dx'). Samples were excited by argon laser at 488 nm, and emission from DOX was collected between 510 nm and 600 nm. MDAMB-231 and MEF cells were grown as described earlier at 60%-70% confluent over coverslips. Samples (2 μg/mL equivalent to DOX) were prepared in 1 mL of cell growth media and were added to cells growing over coverslips. After incubation 0.5 h, the medium was removed, and cells were washed 1× with phosphate-buffered saline (PBS). Cells were then fixed with 4% paraformaldehyde (PFA) for 10 min at room temperature. After 10 min, cells were washed 3× with PBS. FIG. 6 represents examples of confocal images showing cellular uptake of DOX and DOX-conjugate PJL-DOX (mPEG-b-PJL-S-S-DOX, 1dx') in MDAMB-231 cells. FIG. 7 represents an example of fluorescence spectra of free DOX and DOX conjugated with polymer (mPEG-b-PJL-S-S-DOX, 1dx'). FIG. 8 represents examples of confocal images showing cellular uptake of DOX and DOX-conjugate PJL-DOX (mPEG-b-PJL-S-S-DOX, 1dx') in MEF cells.

Figure 9:
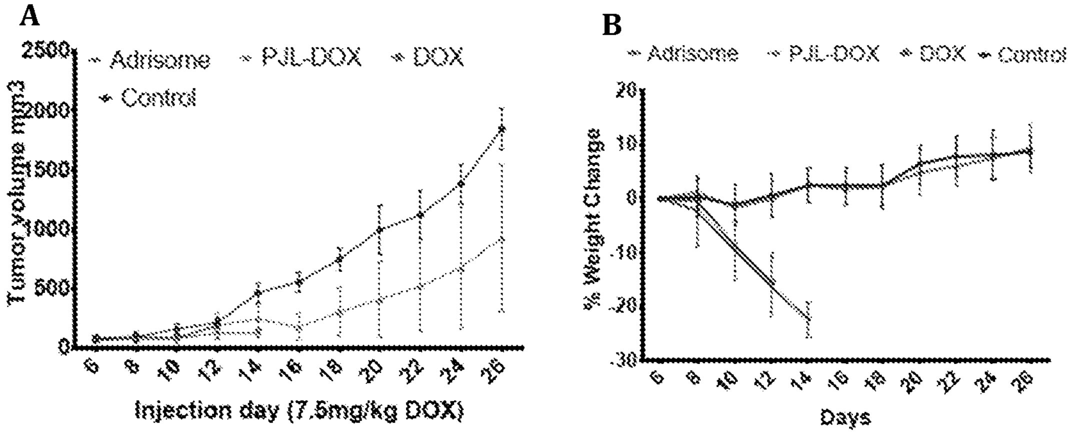
FIG. 9A illustrates an example of tumor volume of murine breast cancer (4T1) cells in Balb/c mice vs injection day when treated with Adrisome (▼), PJL-DOX (mPEG-b-PJL-S-S-DOX (1dx')) (▲), DOX (▬) and control (●), with an equivalent doxorubicin dose of 7.5 mg/kg per animal. Sample injection, on alternate day (total 10 doses), started from $6^{th}$ day after injecting 4T1 cells. All animals of DOX group died after 4 doses whereas Adrisome group animals died after 5 doses.
FIG. 9B illustrates weight change (%) of Balb/c mice vs injection day when treated as above (Adrisome (▼), PJL-DOX (mPEG-b-PJL-S-S-DOX (1dx')) (▲), DOX (■) and control (●).
Figure 10:
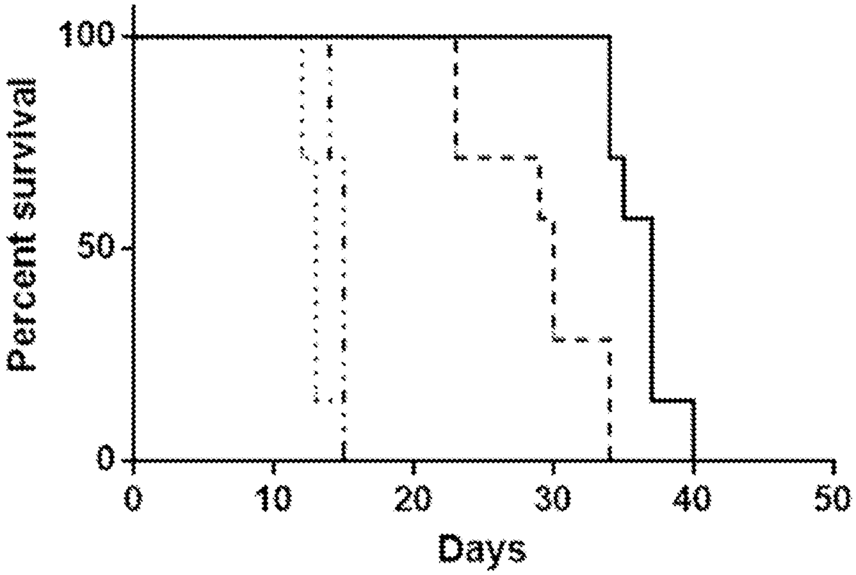
FIG. 10 illustrates an example of survivability (%) of Balb/c mice vs injection day when treated with DOX (•••), Adrisome (—··—··), control (– – –), and PJL-DOX (mPEG-b-PJL-S-S-DOX (1dx')) (——), with an equivalent doxorubicin dose of 7.5 mg/kg of animal. Sample injection, on alternate day (total 10 doses), started from 6$^{th}$ day after injecting 4T1 cells. All animals of DOX group died after 4 doses whereas Adrisome group animals died after 5 doses. This graph indicates that due to low toxicity and precise cytotoxic effect of the DOX conjugate mPEG-b-PJL-S-S-DOX (1dx'), animals receiving PJL-DOX (mPEG-b-PJL-S-S-DOX, 1dx') lived longer than the control group.

In Vivo Studies—Animals:

All animal experiments were done with the approval of Institutional Animal Ethical Committee (IAEC), National Institute of Immunology, New Delhi. Murine breast cancer (4T1) cells (1.5x106) in 200 μL of FBS were injected subcutaneously into the right flanks of 5-week-old female Balb/c mice. Mice were randomized into four groups (6 mice in each group) after they developed a tumor of ~75 $mm^3$. Groups were then subjected to different treatments of (a) PBS (control group); (b) free doxorubicin; (c) PJL-DOX conjugate (mPEG-b-PJL-S-S-DOX (1dx')) and (d) Adrisome (marketed liposomal DOX formulation) with an equivalent doxorubicin dose of 7.5 mg/kg, intravenously through a lateral tail vein on alternate day (total 10 doses). Tumor measurements were made every alternate day using a digital caliper, and tumor volume was calculated using the formula L×B2/2 where L and B are the length and breadth of the tumor. Each mouse was weighed before dosing and weight loss with respect to dosing. The survival study was continued until the last mouse was found live in all the groups. FIG. 9A represents an example of the effect of PBS, DOX, PJL-DOX (mPEG-b-PJL-S-S-DOX (1dx')) and Adrisome on the tumor volume of murine breast cancer (4T1) cells in Balb/c mice vs injection day. FIG. 9B represents an example of the weight change (%) of Balb/c mice vs injection day when treated as above. FIG. 10 represents an example of the effect of PBS, DOX, PJL-DOX (mPEG-b-PJL-S-S-DOX (1dx')) and Adrisome on the survivability (%) of Balb/c mice vs injection day when treated as above.

It will be obvious to a person skilled in the art that, as the technology advances, the inventive concept can be implemented in various ways. The invention and its embodiments are not limited to the examples described above but may vary within the scope of the claims.

The invention claimed is:

1. A polymer comprising at least one repeating unit, wherein the at least one repeating unit has Formula [II]:

[II]

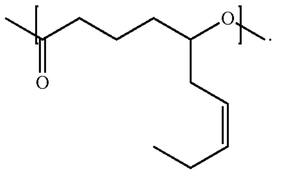

2. The polymer of claim 1, wherein the polymer is a copolymer formed from monomers selected from the group consisting of lactones, carbonates, esters, lactams, alkenes and epoxides.

3. The polymer of claim 2, wherein said monomers are selected from a group consisting of jasmine lactone, lactide, glycolide, caprolactone, decalactone, butyrolactone, ethylene oxide, ethylene, pentadecalactone, hydroxybutanoate, ethylene carbonate, and caprolactam.

4. The polymer of claim 1, wherein the polymer is a copolymer and other repeating unit(s) of the copolymer is/are formed from monomer(s) selected from the group consisting of lactones, carbonates, esters, lactams, alkenes, epoxides, and any combination thereof.

5. The polymer of claim 4, wherein the other repeating unit(s) of the copolymer is/are formed from monomer(s) selected from the group consisting of jasmine lactone, lactide, glycolide, caprolactone, decalactone, butyrolactone, pentadecalactone, hydroxybutanoate, ethylene carbonate, ethylene, ethylene oxide, caprolactam, and any combination thereof.

6. The polymer of claim 4, wherein the other repeating unit of the copolymer is formed from lactide.

7. The polymer of claim 4, wherein the other repeating unit of the copolymer is formed from glycolide.

8. The polymer of claim 1, wherein the polymer is a homopolymer.

9. The polymer according to claim 1, further comprising at least one second repeating unit, the second repeating unit having Formula [I]:

[I]

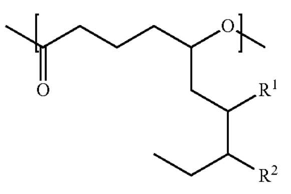

wherein each R1 and R2 is independently selected from a group consisting of H, R6, R21, SR6, SR21, SC(O)R6, SC(O)R21, OR6, OR21, OC(O)R6, OC(O)R21, OC(O)NHR6, OC(O)NHR21, NR6R21, $N(R6)_2$, NHC(O)R6, NHC(O)R21, NHC(O)NHR6, NHC(O)NHR21, $N^+(R6)_3$, $N_3$, $NO_2$, NOR6, CN, and halogen; or R1 and R2, together with the carbon atoms to which they are attached to, form a saturated or partly unsaturated mono-, bi-, tri- or tetracyclic cycloalkyl or heterocycle optionally substituted with one or more SR21, SR6, SC(O)R6, SC(O)R21, OR21, OR6, OC(O)R6, OC(O)R21, OC(O)NHR6, OC(O)NHR21, NR6R21, $N(R6)_2$, $N^+(R6)_3$, R6, R21, halogen, $N_3$, $NO_2$, NOR6, CN, $C_{1-10}$-alkyl, $C_{2-10}$-alkenyl, $C_{2-10}$-alkynyl, $C_{1-5}$-haloalkyl; a mono-, bi-, tri-, tetra- or pentacyclic aryl or heteroaryl optionally substituted with one or more SR21, SR6, SC(O)R6, SC(O)R21, OR21, OR6, OC(O)R6, OC(O)R21, OC(O)NHR6, OC(O)NHR21, NR6R21, $N(R6)_2$, $N^+(R6)_3$, R6, R21, halogen, $N_3$, $NO_2$, NOR6, CN, $C_{1-10}$-alkyl, $C_{2-10}$-alkenyl, $C_{2-10}$-alkynyl, $C_{1-5}$-haloalkyl;

R6 is each independently selected from a group consisting of H, $C_{1-20}$-alkyl, $C_{2-20}$-alkenyl, $C_{2-20}$-alkynyl, $C_{1-10}$-alkylenyl, $C_{1-10}$-haloalkyl, and phenyl;

R21 is each independently selected from $C_{1-10}$-alkylenyl-$CO_2H$, $C_{1-10}$-alkylenyl-OH, $C_{1-10}$-alkylenyl-NHR6, $C_{1-10}$-alkylenyl-SH, $C_{1-10}$-alkylenyl-S—S-$C_{1-10}$-alkylenyl-$CO_2H$, $(CH_2CH_2O)_m$-$C_{1-10}$-alkylenyl-S—S-$C_{1-10}$-alkylenyl-$CO_2H$, $C_{2-20}$-alkynyl, $(CH_2CH_2O)_mH$, $(CH_2CH_2O)_nCH_2CH_2SH$, $(CH_2CH_2O)_nCH_2CH_2N(R6)_2$, $C_{1-10}$-alkylenyl, $C_{1-10}$-haloalkyl, optionally substituted with one or more halogen, $CO_2R6$, OR6, $N(R6)_2$, $N^+(R6)_3$, SR6, $N_3$, $NO_2$, NOR6, CN, $C_{1-10}$-alkyl, $C_{2-10}$-alkenyl, $C_{1-10}$-haloalkyl, $C_{1-10}$-alkylenyl-$CO_2H$, $C_{1-10}$-alkylenyl-OH, $C_{1-10}$-alkylenyl-N(R6) 2, phenyl;

m is an integer from 1 to 100; and n is an integer from 1 to 100;

with the proviso that R1 and R2 are not all hydrogen at the same time.

10. The polymer according to claim 1, wherein the polymer has a Formula that is selected from Formula [If] and Formula [Ig]:

[If]

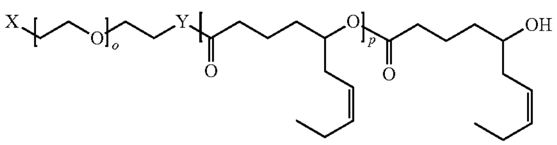

[Ig]

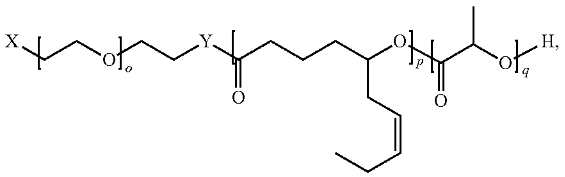

wherein each X is independently selected from a group consisting of OR6, SR6, and $N(R6)_2$;

each Y is independently selected from a group consisting of O, S, and NR6;

wherein R6 is each independently selected from a group consisting of H, $C_{1-20}$-alkyl, $C_{2-20}$-alkenyl, $C_{2-20}$-alkynyl, $C_{1-10}$-alkylenyl, $C_{1-10}$-haloalkyl, and phenyl;

o is an integer from 1 to 1000;

p is an integer from 10 to 2000;

q is an integer from 10 to 2000;

or a salt thereof.

11. The polymer according to claim 1, wherein the polymer has a Formula [Iy]:

[Iy]

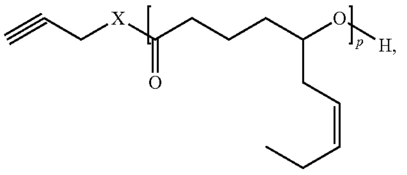

wherein each X is independently selected from a group consisting of O, S, and NR6;

p is an integer from 10 to 2000;

or a salt thereof.

12. A composition comprising a polymer according to claim 1 and at least one active agent, or a salt thereof.

13. The composition of claim 12, wherein the at least one active agent(s) is/are independently covalently attached to or form(s) ionic bond(s) with said polymer.

14. The composition according to claim 12, wherein the at least one active agent(s) is/are independently selected from an active ingredient, an active pharmaceutical ingredient, an antibody, an aptamer, a unit having fluorescence, radioactivity or luminescence, a protein, a peptide, and a flame retardant.

15. The composition according to claim 12, wherein the at least one active agent(s) is/are independently selected from doxorubicin, daunorubicin, epirubicin, idarubicin, paclitaxel, docetaxel, cabazitaxel, camptothecin, cisplatin, fluorescein, fluorescein isothiocyanate (FITC), rhodamine, biotin, folic acid, transferrin, arginylglycylaspartic acid (RGD), rituximab, trastuzumab, cetuximab, bevacizumab, 2-carboxyethyl phenylphosphinic acid (CEPPA), phosphoric acid ($H_3PO_4$), phosphorous acid, 9,10-dihydro-9-oxa-10-phosphaphenanthrene-10-oxide, and fludeoxyglucose ($[^{18}F]$FDG), and any derivative thereof.

16. A method for producing a polymer or a salt thereof, the method comprising:

i) providing jasmine lactone as a jasmine lactone monomer, ii) optionally modifying at least part of the jasmine lactone monomers of i) with at least one suitable reagent to form a modified jasmine lactone monomer with Formula (III),

[III]

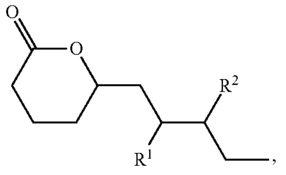

wherein R1 and R2 are as defined as in claim 9, iii) subjecting the jasmine lactone monomer of i) and/or the modified jasmine lactone monomer of ii) to a polymerization reaction to form a polymer.

17. The method according to claim 16, wherein the polymerization reaction of iii) is performed in the presence of at least one further monomer to form a copolymer.

18. The method according to claim 16, wherein the formed polymer or the formed copolymer is further reacted with at least one suitable reagent capable of reacting or interacting with the formed polymer or the formed copolymer to form a modified polymer or a modified copolymer, respectively.

19. The method according to claim 16, wherein the formed polymer or the formed copolymer is further reacted with at least one active agent to form a composition.

20. The method according to claim 16, wherein at least a part of the jasmine lactone monomer of i) and/or the modified jasmine lactone monomer of ii) is reacted with at least one active agent before or during the polymerization reaction of iii) to form a functionalized jasmine lactone and/or a functionalized modified jasmine lactone, respectively, and subjecting the formed functionalized jasmine lactone and/or the functionalized modified jasmine lactone to a polymerization reaction to form a composition.

21. The method according to claim 20, wherein the formed functionalized jasmine lactone and/or the functionalized modified jasmine lactone is subjected to a polymerization reaction in the presence of at least one further monomer to form a composition.

22. The method according to claim 19, wherein the at least one active agent(s) is/are independently selected from an active ingredient, an active pharmaceutical ingredient, an antibody, an aptamer, a unit having fluorescence, radioactive or luminescence, a protein, a peptide, and a flame retardant.

23. The method according to claim 19, wherein the active agent comprises doxorubicin, daunorubicin, epirubicin, idarubicin, paclitaxel, docetaxel, cabazitaxel, camptothecin, cisplatin, fluorescein, fluorescein isothiocyanate (FITC), rhodamine, biotin, folic acid, transferrin, arginylglycylaspartic acid (RGD), rituximab, trastuzumab, cetuximab, bevacizumab, 2-carboxyethyl phenylphosphinic acid (CEPPA), phosphoric acid ($H_3PO_4$), phosphorous acid, 9,10-dihydro-9-oxa-10-phosphaphenanthrene-10-oxide, and fludeoxyglucose ($[^{18}F]$ FDG).

24. A pharmaceutical composition comprising one or more polymer as claimed in claim 1 or an effective amount of one or more composition thereof, in combination with one or more other active ingredient(s).

25. The pharmaceutical composition as claimed in claim 24, together with one or more pharmaceutically acceptable excipient(s).

26. A pharmaceutical composition as claimed in claim 24 for use as a medicament.

27. The method according to claim 18, wherein the formed polymer, the formed copolymer, the formed modified polymer or the formed modified copolymer is further reacted with at least one active agent to form a composition.

* * * * *